United States Patent
Landau

(10) Patent No.: US 11,311,478 B2
(45) Date of Patent: Apr. 26, 2022

(54) PREBIOTIC AND PROBIOTIC COOKIE PREPARATION

(71) Applicant: Uplift Food, Brooklyn Heights, NY (US)

(72) Inventor: Kara Landau, New York, NY (US)

(73) Assignee: Uplift Food, Brooklyn Heights, NY (US)

( * ) Notice: Subject to any disclaimer, the term of this patent is extended or adjusted under 35 U.S.C. 154(b) by 0 days.

(21) Appl. No.: 16/913,613

(22) Filed: Jun. 26, 2020

(65) Prior Publication Data
US 2021/0401737 A1     Dec. 30, 2021

(51) Int. Cl.

| | |
|---|---|
| *A61K 9/00* | (2006.01) |
| *A61K 47/36* | (2006.01) |
| *A61K 47/44* | (2017.01) |
| *A61K 35/742* | (2015.01) |
| *A61K 36/48* | (2006.01) |
| *A23L 33/125* | (2016.01) |
| *A23L 33/135* | (2016.01) |
| *A23L 33/22* | (2016.01) |
| *A23L 33/115* | (2016.01) |
| *A23L 33/00* | (2016.01) |
| *A21D 2/18* | (2006.01) |
| *A21D 2/16* | (2006.01) |
| *A21D 6/00* | (2006.01) |
| *A21D 13/045* | (2017.01) |
| *A21D 13/14* | (2017.01) |
| *A23L 9/20* | (2016.01) |
| *A61K 47/10* | (2017.01) |

(52) U.S. Cl.
CPC ............ *A61K 9/0056* (2013.01); *A21D 2/165* (2013.01); *A21D 2/186* (2013.01); *A21D 6/006* (2013.01); *A21D 13/045* (2017.01); *A21D 13/14* (2017.01); *A23L 9/24* (2016.08); *A23L 33/115* (2016.08); *A23L 33/125* (2016.08); *A23L 33/135* (2016.08); *A23L 33/22* (2016.08); *A23L 33/40* (2016.08); *A61K 35/742* (2013.01); *A61K 36/48* (2013.01); *A61K 47/10* (2013.01); *A61K 47/36* (2013.01); *A61K 47/44* (2013.01); *A23V 2002/00* (2013.01)

(58) Field of Classification Search
CPC .... A61K 9/0056; A61K 35/742; A61K 36/48; A61K 47/10; A61K 47/36
See application file for complete search history.

(56) References Cited

U.S. PATENT DOCUMENTS

| | | |
|---|---|---|
| 7,101,565 B2 | 9/2006 | Monte |
| 9,463,169 B2 | 10/2016 | Heiman et al. |
| 2014/0302223 A1 | 10/2014 | Skelding et al. |
| 2015/0037469 A1* | 2/2015 | Folz ...................... A21D 13/22 |
| | | 426/103 |
| 2016/0213612 A1* | 7/2016 | Lefkowitz .............. A23G 3/343 |
| 2018/0318323 A1 | 11/2018 | Roman et al. |
| 2019/0008824 A1 | 1/2019 | Blanchard et al. |

FOREIGN PATENT DOCUMENTS

| | | | | |
|---|---|---|---|---|
| WO | WO-2013077900 A1 * | 5/2013 | ............... | A23G 3/46 |
| WO | 2018115744 A1 | 6/2018 | | |

OTHER PUBLICATIONS

Turner (Our Grain-Free Life, https://ourgrainfreelife.com/2016/07/aip-oatmeal-raisin-cookies/, Jul. 2016; referred to as "Our Grain-Free") (Year: 2016).*
Kumalasari et al (Cytotechnology, 2012, vol. 64, pp. 131-137) (Year: 2012).*
Llavata et al (Foods, 2020, vol. 9, pp. 1-15) (Year: 2020).*
Queen Keto (Sugar Free Lemon and Blueberry Double Baked Cookies, https://queenketo.com/sugar-free-lemon-blueberry-double-baked-cookie/, Jan. 2017) (Year: 2017).*
Irena Macri (10 Paleo flour alternatives, https://irenamacri.com/10-paleo-flour-alternatives/, Mar. 9, 2019) (Year: 2019).*
CraftyBaking (Basic Cookie Ingredients, 2000, https://www.craftybaking.com/learn/baked-goods/cookies/ingredients) (Year: 2000).*
Baking Sense (Function of Fats in Baking, 2020, https://www.baking-sense.com/2017/03/29/baking-ingredients-butter-fat/) (Year: 2020).*
Hancocks (NUTRA Ingredients.com, Dec. 19, 2019, https://www.nutraingredients.com/Article/2019/12/18/Gut-Happy-Cookie-founder-reveals-tips-for-teaming-up-with-global-snacks-giant) (Year: 2019).*

* cited by examiner

*Primary Examiner* — Mark V Stevens
(74) *Attorney, Agent, or Firm* — Gearhart Law LLC; David Postolski, Esq.

(57) ABSTRACT

A cookie that provides a prebiotic effect and/or a probiotic effect to a consumer is described. The cookie fails to contain refined sugars, synthetic vitamins, genetically modified organisms (GMOs), artificial sweeteners, and artificial preservatives. The cookie comprises at least two baked food compositions formed into a biscuit. Each of the at least two baked food compositions contains a polyphenol, a resistant starch, and a prebiotic soluble fiber. A crème filing is sandwiched between the at least two baked food compositions. The crème filing comprises a resistant starch, a nut butter, a vegetable fat, and spores of a probiotic bacterium. Consumption of the cookie increases *Lactobacillus bulgaricus* and butyrate in the consumer.

4 Claims, 28 Drawing Sheets

| Active Ingredients Total mg (40g serve) | Cooked Ingredients (Base + Meal) | Uncooked Ingredients (Crème) | TOTAL |
|---|---|---|---|
| Kiwi Fruit Powder (T52280OFMC) | 16.8 | - | 16.8 |
| Org Toasted Lupin (T35OTMC) | 15,984.1 | - | 15,984.1 |
| Org Tigernut Flour (T12116620MC) | 1,644.4 | - | 1,644.4 |
| FIBERSMART Powder (T6079OMC) | 4,212.9 | 2,106.5 | 6,319.4 |
| Vitafiber (IMO) (TVFTAPMC) | 2,677.1 | - | 2,677.1 |
| Probiotic Powder (T3073215 6MC) | - | 74.5 | 74.5 |
| TOTAL (mg) | 24,535.4 | 2,181.0 | 26,716.3 |

FIG. 1

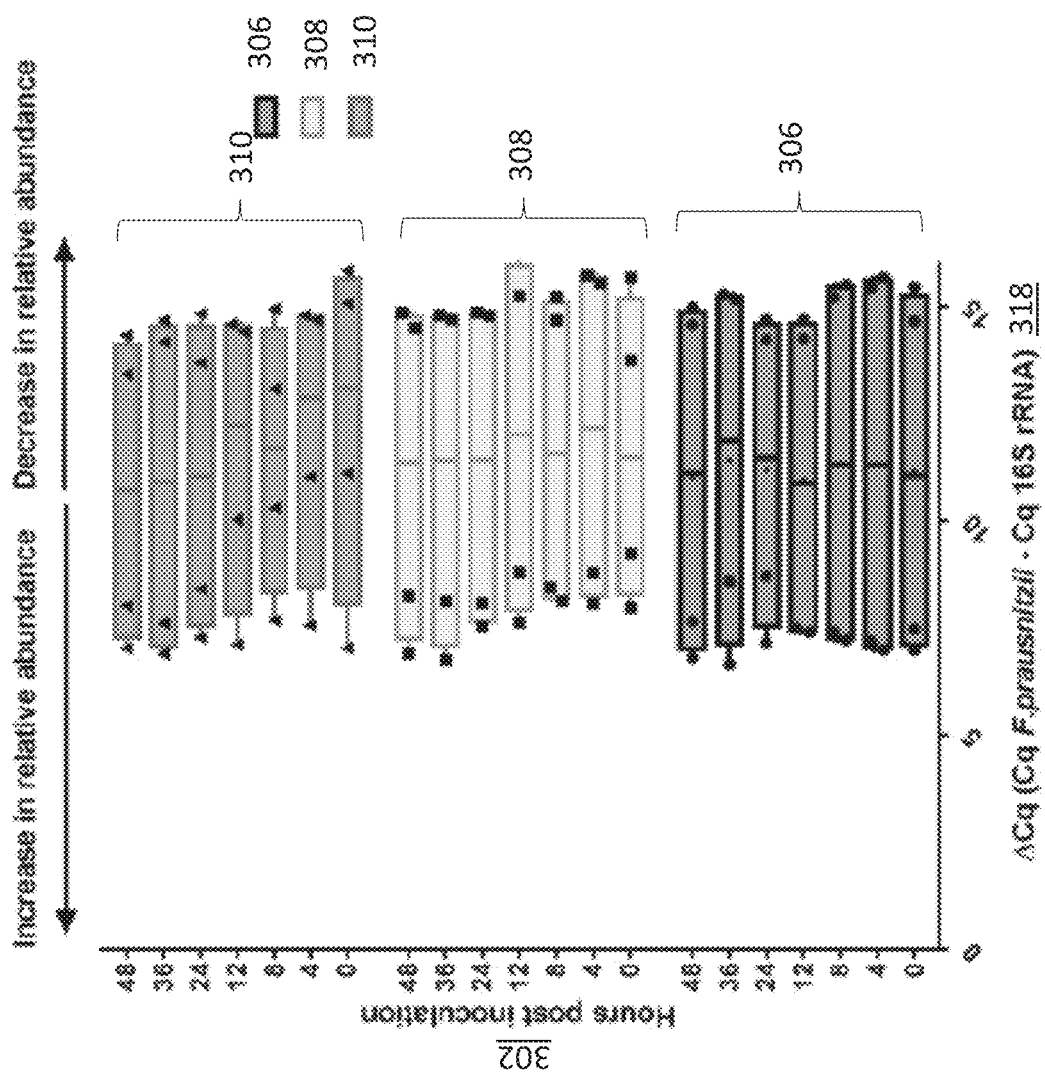

PREBIOTIC AND PROBIOTIC COOKIE PREPARATION

CROSS-REFERENCE TO RELATED APPLICATIONS

This application is a U.S. Non-Provisional Patent Application that claims priority to U.S. Provisional Patent Application No. 62/868,960 filed on Jun. 30, 2019, the contents of which are hereby incorporated by reference in their entirety.

FIELD OF THE EMBODIMENTS

This invention relates to edible compositions, e.g., cookies, comprising prebiotic and probiotic blends for improved gut health.

BACKGROUND OF THE EMBODIMENTS

At the beginning of the last century, the Russian immunologist and Nobel Prize Laurate, Elie Metchnikoff, discovered that the consumption of live bacteria (*Lactobacillus bulgaricus*) in yogurt or fermented milk had beneficial effects on the gastrointestinal tract of humans (see, e.g., Metchinikoff, E., Prolongation of Life, William Heinermann, London 1910). Defined by the Food and Agriculture Organization (FAO) of the United Nations World Health Organization (WHO) as "live microorganisms which when administered in adequate amounts confer a health benefit to the host," probiotics are now widely available in the form of foods such as dairy products, juices, capsules, drops, and powders. Health benefits of probiotics include digestive health, normalization of bowel movements, strengthening of the immune system, improved mood, improved heart health, control of cholesterol, neutralization of toxins, countering of allergies and skin problems, as well as the prevention of yeast and fungal infections. Prebiotic formulations that promote the proliferation of probiotic microorganisms in the intestinal tract that confer the aforementioned health benefits are being actively sought. For example, the National Institutes of Health (NIH) is funding new research into how prebiotics could be used to help manage chronic gastrointestinal disorders such as inflammatory bowel disease (IBD) and irritable bowel syndrome (IBS). Thus, there is an on-going need for improved prebiotic and probiotic compositions.

The present invention discloses a cookie product that addresses the need for improved prebiotic and probiotic formulations that promote gut health.

Examples of related art are described below:

U.S. Published Patent Application No. 2018/0318323 A1 relates to various embodiments of a gut microbiome modulating composition comprises a blend of a polyphenol and an oligosaccharide. Various embodiments of the polyphenol may comprise at least approximately 5% by weight chlorogenic acid. Various embodiments of the oligosaccharides may be standardized to a degree of polymerization of at least three to reduce digestibility. Administration of an effective amount of the gut microbiome modulating composition to a person or animal may stimulate the growth of at least one of *Akkermansia muciniphila*, *Lactobacillus*, and *Bifidobacterium* bacteria in the colon, which may reduce permeability of the colon, increases short chain fatty acid production in the colon, and/or modulate causes immunomodulation of human colon cells. The gut microbiome modulating composition may provide protective effects against obesity-related chronic diseases.

U.S. Pat. No. 9,463,169 B2 relates to a formulation to increase the ratio of gastrointestinal microbiota in phylum Bacteroidetes to microbiota of Firmicutes phylum preferably includes about 20-60 mg/kg of body weight of fermentable fiber, about 10-30 mg/kg of body weight of beta glucan and about 20-60 mg/kg of body weight of blueberry extracts or any fruit or berry ingredient preparation containing similar phenolics. This formulation is preferably used to control body weight, body composition, and blood glucose regulation, preferably in humans, and is preferably administered orally, preferably twice per day.

WO 2018/115744 A1 relates to a composition for feeding a non-human mammal, advantageously a herbivore, comprising a mixture of co-products of cereal distillation or of beer production with or without solubles (DDG and DDGS), of concentrated cereal solubles (CDS), of prebiotic fibers, of probiotics, of amino acids, of proteins, of omega 3, of lignan, and of digestive enzymes. It also relates to a nutritional feed bucket comprising said composition and to the use thereof for improving the zootechnical performance levels of a non-human, advantageously herbivorous, mammal, for increasing the digestibility of solids and of fibers, in particular of fodder and concentrates, and/or improving the consumption index and/or the dietary efficiency and/or promoting weight gain and/or increasing the intensity of microbial metabolism and fermentation and/or reducing gas emission, in particular methane emission, and/or inhibiting the protozoa of the flora and/or decreasing protein degradation and/or directing fermentations towards the production of volatile fatty acids, in particular towards propionic acid, in a non-human, advantageously herbivorous, mammal.

U.S. Published Patent Application No. 2014/0302223 A1 discloses nutritional compositions comprising a soluble viscous fiber and a polyphenol-containing plant extract. The viscosity of the nutritional compositions may be adjusted and controlled without varying the concentration of the soluble viscous fiber in the composition by including the polyphenol-containing plant extract.

U.S. Published Patent Application No. 2019/0008824 A1 relates to a composition comprising at least one cocoa polyphenol and soluble dietary fiber for use in the prevention or treatment of a disorder associated with an above-normal number of granulocytes in a tissue.

U.S. Pat. No. 7,101,565 B2 discloses a prebiotic composition comprising a probiotic and prebiotic, and method of delivering a probiotic, prebiotic or composition directly into the intestinal tract of a mammal are disclosed. The probiotic is any beneficial bacteria and the prebiotic is a substance beneficial to a probiotic. Most preferably, the prebiotic includes a mucopolysaccharide. The method preferably involves delivering the prebiotic, probiotic or composition via a delivery tube, such as an enteral feeding tube, directly to a position downstream of the stomach, most preferably to the jejunum.

None of the art described above teaches a cookie product for the oral consumption and delivery of an optimized prebiotic formulation or prebiotic and prebiotic formulation to the gastrointestinal tract.

SUMMARY OF THE EMBODIMENTS

The present invention and its embodiments relate to edible compositions, such as cookies, comprising prebiotic and probiotic blends for improved gut health.

A first embodiment of the present invention describes a cookie for improving gut health. The cookie fails to contain refined sugars, synthetic vitamins, genetically modified organisms (GMOs), artificial sweeteners, and artificial preservatives. The cookie includes a baked food composition. The baked food composition contains a polyphenol, a resistant starch, and a prebiotic soluble fiber. In other examples, the prebiotic soluble fiber may be lupin flour. In some examples, the prebiotic soluble fiber may be an isomalto-oligosaccharide (IMO), among other components not explicitly listed herein. The resistant starch may be a resistant dextrin, such as Fibersmart™, and/or tigernut flour, among other components not explicitly listed herein. The polyphenol may be a kiwi fruit powder, among other components not explicitly listed herein. In some examples, the baked food composition is a biscuit.

Moreover, in some examples, the prebiotic soluble fiber is present in a range of approximately 15% to approximately 25% (w/w) of the baked food composition and the polyphenol is present in a range of approximately 0.1% to approximately 5% (w/w) of the baked food composition. The resistant starch is present in a range of approximately 15% to approximately 25% (w/w) of the cookie.

The cookie may also include a crème filling sandwiched between two of the biscuits. The crème filing contains a resistant starch, a nut butter, a vegetable fat, and spores of a probiotic bacterium. In some examples, the spores of the probiotic bacterium comprise spores of *Bacillus coagulans*. The crème filing fails to contain refined sugars, synthetic vitamins, genetically modified organisms (GMOs), artificial sweeteners, and artificial preservatives.

It should be appreciated that consumption of the cookie provides a prebiotic effect and/or a probiotic effect to a consumer. In examples, consumption of the cookie increases *Lactobacillus bulgaricus, Bacillus coagulans, Collinsella aerofaciens*, Hippurate, Erysipelotrichia, and/or Streptophyta in the consumer. In some examples, consumption of the cookie increases *Lactobacillus bulgaricus* and butyrate in the consumer.

A second embodiment of the present invention describes a method for making a cookie that provides a prebiotic effect and/or a probiotic effect to the consumer. The method includes: blending dry ingredients comprising a polyphenol, a resistant starch, and a prebiotic soluble fiber with vegetable fat; mixing in water until glomeration and formation of a dough; and baking the dough to produce a baked food composition. The prebiotic soluble fiber may be lupin flour and/or isomalto-oligosaccharide (IMO), among other examples not explicitly listed herein. The resistant starch may be a resistant dextrin, such as Fibersmart™, and/or tigernut flour. The polyphenol may be the kiwi fruit powder.

In some examples, the baked food composition is a biscuit. The method may further comprise: sandwiching a crème filling between two of the biscuits to produce a cookie. The crème filing may be produced by: mixing vegetable fats to form a first mixture; mixing nut butter with a resistant starch to form a second mixture; and blending the first and second mixtures with a natural flavor and probiotic spores until glomeration of the crème filling. The probiotic spores may comprise spores of *Bacillus coagulans*.

A third embodiment of the present invention describes a cookie that provides a prebiotic effect and/or a probiotic effect to the consumer. The cookie fails to contain refined sugars, synthetic vitamins, genetically modified organisms (GMOs), artificial sweeteners, and artificial preservatives. The cookie comprises at least two baked food compositions formed into a biscuit and a crème filing sandwiched between the at least two baked food compositions. Each of the at least two baked food compositions contains a polyphenol comprising the kiwi fruit powder, a resistant starch comprising a resistant dextrin (e.g., Fibersmart™) and/or tigernut flour, and a prebiotic soluble fiber comprising lupin flour and/or an isomalto-oligosaccharide (IMO), among other examples not explicitly listed herein. The crème filing comprises a resistant starch, a nut butter, a vegetable fat, and spores of a probiotic bacterium. The spores of the probiotic bacterium comprise spores of *Bacillus coagulans*. Consumption of the cookie increases *Lactobacillus bulgaricus, Bacillus coagulans, Collinsella aerofaciens*, Hippurate, Erysipelotrichia, and/or Streptophyta in the consumer. In some examples, consumption of the cookie increases *Lactobacillus bulgaricus* and butyrate in the consumer.

In general, the present invention succeeds in conferring the following benefits and objectives.

It is an object of the present invention to deliver a cookie that provides a prebiotic effect to a consumer.

It is an object of the present invention to deliver a cookie that provides a probiotic effect to the consumer.

It is an object of the present invention to provide a cookie that increases *Lactobacillus bulgaricus* and butyrate in the consumer post-consumption.

It is an object of the present invention to provide a cookie comprising a baked food composition formed into a biscuit, the baked food composition containing a polyphenol, a resistant starch, and a prebiotic soluble fiber.

It is an object of the present invention to provide a crème filing comprising a resistant starch, a nut butter, a vegetable fat, and spores of a probiotic bacterium.

It is an object of the present invention to provide a cookie comprising at least two baked food compositions formed into the biscuit and the crème filing sandwiched between the at least two baked food compositions (e.g., biscuits), where each of the at least two baked food compositions contain a polyphenol, a resistant starch, and a prebiotic soluble fiber and the crème filing comprises a resistant starch, a nut butter, a vegetable fat, and spores of a probiotic bacterium.

BRIEF DESCRIPTION OF THE DRAWINGS

FIG. 1 depicts an exemplary list of components included in a prebiotic/probiotic cookie formulation, according to at least some embodiments disclosed herein.

FIG. 10 depicts a graphical representation of a relative abundance of *Faecalibacterium prausnitzii* in a bioreactor after addition of a formulation, according to at least some embodiments disclosed herein.

DESCRIPTION OF THE PREFERRED EMBODIMENTS

Figure 2:
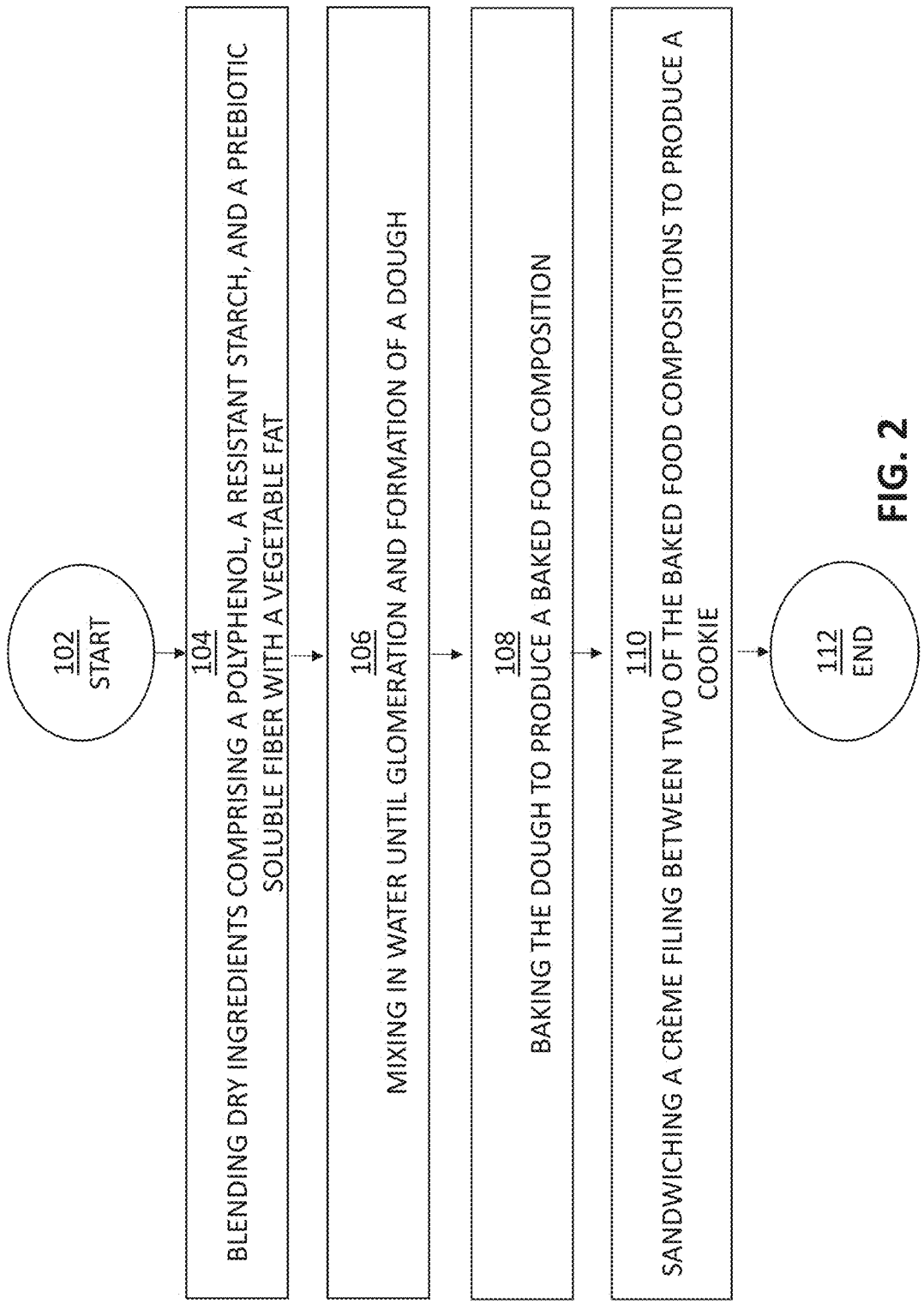
FIG. 2 depicts a block diagram of a method for making a baked food composition (e.g., a biscuit) for improving gut health, according to at least some embodiments disclosed herein.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

As used herein, the singular forms "a," "an," and "the," are intended to include the plural forms as well, unless the context clearly indicates otherwise.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, an "embodiment" means that a particular feature, structure or characteristic is included in at least one or more manifestations, examples, or implementations of this invention. Furthermore, the particular features, structures or characteristics may be combined in any suitable manner, as would be apparent to a person skilled in the art. Combinations of features of different embodiments are all meant to be within the scope of the invention, without the need for explicitly describing every possible permutation by example. Thus, any of the claimed embodiments can be used in any combination.

The phrase "and/or," as used herein in the specification and in the claims, should be understood to mean "either or both" of the elements so conjoined, e.g., elements that are conjunctively present in some cases and disjunctively present in other cases. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

When the term "about" is used in conjunction with a numerical range, it modifies that range by extending the boundaries above and below those numerical values. In general, the term "about" is used herein to modify a numerical value above and below the stated value by a variance of 20%, 10%, 5%, or 1%. In certain embodiments, the term "about" is used to modify a numerical value above and below the stated value by a variance of 10%. In certain embodiments, the term "about" is used to modify a numerical value above and below the stated value by a variance of 5%. In certain embodiments, the term "about" is used to modify a numerical value above and below the stated value by a variance of 1%.

When a range of values is listed herein, it is intended to encompass each value and sub-range within that range. For example, "1-5 ng" is intended to encompass 1 ng, 2 ng, 3 ng, 4 ng, 5 ng, 1-2 ng, 1-3 ng, 1-4 ng, 1-5 ng, 2-3 ng, 2-4 ng, 2-5 ng, 3-4 ng, 3-5 ng, and 4-5 ng.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

As used herein, unless stated otherwise, the term "subject" and the term "patient" are used interchangeably herein. In certain embodiments, the subject is a human. In certain embodiments, the human is a pediatric human. In certain embodiments, the subject is an adult human. In certain embodiments, a subject is a human suffering from a gastrointestinal disorder, such as irritable bowel syndrome (IBS) or colitis. In other examples, the subject is an animal.

The terms "effective amount" or "therapeutically effective amount" as used herein, refer to a sufficient amount of at least one agent being administered which achieve a desired result, e.g., to relieve to some extent one or more symptoms of a disease or condition being treated. In certain instances, the result is a reduction and/or an alleviation of the signs, symptoms, or causes of a disease, or any other desired alteration of a biological system. In some embodiments, the effective amount is a dose that is generally effective in alleviating, reducing, noticeably reducing, or eliminating, symptoms associated with a gastrointestinal disorder. In certain instances, an "effective amount" for therapeutic uses is the amount of the composition comprising an agent as set forth herein required to provide a clinically significant decrease in the disorder. An appropriate "effective" amount in any individual case is determined using any suitable technique, such as dose escalation studies.

As used herein, the terms "treat," "treatment" or "treating" refer to therapeutic treatments, wherein the object is to reverse, alleviate, ameliorate, inhibit, slow down or stop the progression or severity of a gastrointestinal disorder. The term "treating" includes reducing or alleviating at least one adverse effect or symptom of the gastrointestinal disorder. Treatment is generally "effective" if one or more symptoms or clinical markers are decreased. Alternatively, treatment is "effective" if the progression of the disorder is reduced or halted. That is, "treatment" includes not just the improvement of symptoms or markers, but also a cessation of, or at least slowing of, progress or worsening of symptoms compared to what would be expected in the absence of treatment. The term "treatment" also includes providing relief from the symptoms or side-effects of a disorder, e.g. a gastrointestinal disorder.

Prebiotic Constituent

As used herein, a "prebiotic" refers to a nutritional supplement for a probiotic organism, e.g. probiotic bacteria. Prebiotics are food ingredients, for example, oligosaccharides, that are non-digestible by a subject (e.g., by a mammal, such as a human), but are able to stimulate the growth or activity of one or more beneficial microorganisms. In certain embodiments, a prebiotic organism can inhibit the growth or the activity of one or more pathogenic bacteria. In certain embodiments, a prebiotic organism can selectively stimulate the growth and/or the activity of one or of a limited number of bacteria in the subject.

For a food ingredient to be classified as a prebiotic, it should neither be hydrolyzed, nor absorbed in the upper gastrointestinal tract. Moreover, for a food ingredient to be classified as a prebiotic, it must be selectively fermented by one or a limited number of potentially beneficial bacteria commensal to the colon, such as lactobacilli and bifidobacteria, which are stimulated to grow and/or become metabolically activated. Additionally, for a food ingredient to be classified as a prebiotic, it must be able to alter the colonic microflora towards a healthier composition, by increasing, for example, numbers of saccharolytic species while reducing the number of harmful bacteria (e.g., clostridia and/or *Escherichia coli*).

Exemplary prebiotics can be found in plants, like the Jerusalem artichoke, chicory root, apples, bananas, asparagus, onions, leeks, and garlic. Moreover, some yogurts, cereals, and breads contain prebiotic additives, like galacto-oligosaccharides (GOS), fructo-oligosaccharides (FOS), and inulin.

The present disclosure describes a baked food product or composition. The baked food product or composition contains no refined sugars, synthetic vitamins, genetically modified organisms (GMOs), artificial sweeteners, or artificial preservatives. In examples, the baked food product or composition may comprise one or more organic ingredients or components. In some examples, the baked food product is a biscuit. The baked food product may comprise a blend of prebiotic soluble fibers, a polyphenolic compound, and a resistant starch, among other components.

In certain embodiments, the prebiotic soluble fibers may comprise a dry flour blend of two or more different types of prebiotics fibers that are soluble in water. In certain embodiments, the prebiotic soluble fibers comprise a dry flour blend of three different prebiotic soluble fibers that are formulated to promote a probiotic, e.g., a bifidogenic, response. In some examples, the prebiotic soluble fibers comprises approximately 15-25% (w/w) of the baked food composition.

One study evaluated the raffinose family of oligosaccharides (RFOs) isolated from lupin seeds (*Lupinus albus* var. Multolupa) for bifidogenic effects during the manufacture of probiotic fermented milk. See, Cristina Martinez-Villaluenga, et al., "Raffinose Family of Oligosaccharides From Lupin Seeds as Prebiotics: Application in Dairy Products," J. Food. Prot., 2005, 68(6), Pages 1246-52. A mixed starter inoculum was composed of *Bifidobacterium lactis* Bb-12 and *Lactobacillus acidophilus* (1:1). Lupins are a rich source of RFOs that can be used as functional food ingredients. According to this study, the addition of RFOs to milk increased *Bifidobacterium lactis* Bb-12 and *Lactobacillus acidophilus* populations at the final fermentation time compared with controls. Final fermentation products were positively affected by addition of RFOs, and the time of fermentation was reduced from 12 to 10 hours. When RFOs were added to milk, they were preferentially used as a carbon source (57.7%) compared with lactose (23.7%) at the end of fermentation. These results of this study suggest that the eventual choice of *Bifidobacterium lactis* Bb-12 and *Lactobacillus acidophilus* in a mixed culture at a 1:1 ratio and addition of RFOs to produce a fermented milk product would have the advantages of rapid growth and acidificationrate and would likely increase the probiotic effect of the final functional product. Based on this study, exemplary blends of prebiotic soluble flours described herein comprise lupin flour.

In certain embodiments, a prebiotic formulation for improved digestive health may comprise an isomalto-oligosaccharide (IMO) as a prebiotic soluble fiber. An example IMO is VitaFiber™, which is a commercially available prebiotic, a non-genetically modified organism (GMO), and a corn-free dietary soluble fiber comprising isomalto-oligosaccharide sourced from the root of the tapioca plant. VitaFiber™ is minimally processed with no preservatives, gluten, or allergens. It should be appreciated that the prebiotic soluble flours are not limited to lupin flour and/or the IMO, and other prebiotic soluble fibers not explicitly listed herein are contemplated.

The baked food product or composition may also comprise a polyphenolic compound. In some examples, the polyphenol comprises approximately 0.1-5% (w/w) of the baked food composition. The polyphenolic compound can be used to modify the taste and/or flavor of edible consumables, that is, finished compound foods and beverages, by incorporating therein an effective amount of a monomeric or oligomeric polyphenol (MPP and OPP).

In certain embodiments, polyphenolic compounds may include proanthocyanidins (PCs) including monomeric proanthocyanidins (MPCs) and oligomeric proanthocyanidins (OPCs), and other phenolic based monomers and oligomers usually improving the flavor, taste, mouthfeel and character, that is, the sensory qualities of various food systems and selected food ingredients. In certain embodiments, the polyphenolic compound comprises whole kiwi fruit powder (such as Livaux™ from Zespri KiwiFruit). Without being held to any particular theory, it is believed the fiber of the Kiwifruit provides the prebiotic benefit, and its polyphenolic compound supports gut transit.

The baked food product or composition may also comprise a resistant starch. In some examples, the resistant starch comprises approximately 15-25% (w/w) of the baked food composition. Enzyme resistant starch is an indigestible form of starch that can behave like a dietary fiber. See, Cihadiye Candal, et al., "The effects of different processes on enzyme resistant starch content and glycemic index value of wheat flour and using this flour in biscuit production," Journal of Food Science and Technology, 2019, 56, Pages 4110-4120. More specifically, enzyme resistant starch is a fraction of starch not digested in the small intestine of healthy individuals. Microflora may partially ferment certain types of resistant starch in the large bowel. Furthermore, enzyme resistant starch may be defined as the sum of starch and products of starch degradation not absorbed in the small intestine, and it may be classified into four types. See, U.S. Pat. No. 6,613,373 B2, granted on Sep. 2, 2003, the contents of which are incorporated by reference in its entirety.

Type I resistant starch is physically inaccessible starch and is locked in the plant cell. Type I resistant starch is a fraction which can be found in foodstuffs with partially milled grains and seeds and legumes. Native granular starch found in uncooked ready-to-eat starch-containing foods, such as in bananas, is classified as type II resistant starch. Enzyme susceptibility of type II resistant starch is reduced by the high density and the partial crystallinity of the granular starch. The amount of type I and type II resistant starches is generally less than about 12% by weight, based upon the total amount of uncooked or raw starch contained in the starch source. However, the type I and type II resistant starches have low melting points, do not survive a baking process, and do not exhibit good baking functionality. See, U.S. Pat. No. 6,613,373 B2.

Starch may be treated to obtain an indigestible starch fraction. Depending upon the type of treatment, a type III resistant starch or a type IV resistant starch may be produced. An indigestible starch fraction which forms after certain heat-moisture treatments of the starch, which may be present in, for example, cooled, cooked potatoes, and canned peas or beans, is type III enzyme-resistant starch. In type IV resistant starch, the enzyme resistance is introduced by chemically modifying or thermally modifying the starch. The modification may be the formation of glycosidic bonds, other than alpha-(1-4) or alpha-(1-6) bonds, by heat treatment. Formation of these other glycosidic bonds may reduce the availability of starch for amylolitic enzymes. See, U.S. Pat. No. 6,613,373 B2.

Exemplary forms of resistant starch include, but are not limited to, tigernut flour, green banana flour, and tapioca fiber. Tigernut is a small root vegetable that grows in Northern Africa and the Mediterranean. Tigernut flour is naturally gluten-free. Further, tigernuts contain a variety of nutrients and beneficial plant compounds. Tigernuts are high in fiber, iron, potassium, protein, magnesium, zinc, vitamin E, and vitamin C. Tigernuts are also a rich source of antioxidants, which are beneficial compounds that protect one's body against aging and diseases. Tigernuts also contain antinutrients, such as phytates, oxalates, saponins and tannins, which can reduce nutrient absorption in your gut. Germinating or roasting the tubers prior to eating reduces their antinutrient levels, making it easier for your body to absorb and use the many nutrients they contain.

Tigernuts may also promote a healthy digestion in various ways. First, tigernuts are high in insoluble fiber, which passes through ones gut without being digested. Tigernuts are also presumed to contain resistant starch, a type of fiber that can feed the friendly bacteria in one's gut, helping digestion run smoothly. Moreover, tigernuts may contain enzymes, such as catalases, lipases and amylases, which help break down foods in one's gut, relieving gas, indigestion, and diarrhea.

Further, animal studies show that tigernut extract may help reduce blood sugar levels. This may, in large part, be due to the high fiber content of the tubers which may slow down the absorption of sugar in the gut. See, Chukwuma Ekeanyanwu, et al., "The Phytochemical Composition and Some Biochemical Effects of Nigerian Tigernut (*Cyperus esculentus* L.) Tuber," Pakistan Joural of Nutrition, 2010, 9(7), Pages 709-715. Tigernuts are also rich in the amino acid arginine, which may increase insulin production and sensitivity, both of which are important for blood sugar control. See, Diego Soares Carvalho, et al., "L-Arginine Supplementation Improves Insulin Sensitivity and Beta Cell Function in the Offspring of Diabetic Rats Through AKT and PDX-1 Activation," Eur. J. Pharmacol., 2016, 791, Pages 780-787; and Makoto Umeda, et al., "Arginine-induced insulin secretion in endoplasmic reticulum," Biochemical and Biophysical Research Communications, 2015, 466(4), Pages 717-722. Moreover, test-tube studies show that tigernut extract may inhibit the action of carb-digesting enzymes in one's gut. As a result, less sugar may be absorbed from ones gut in a way similar to the action of some blood-sugar-lowering diabetic medications. This is thought to potentially lower blood sugar levels, though more research in humans is needed. See, Saheed Sabiu, et al., "Kinetics of Modulatory Role of *Cyperus Esculentus* L. on the Specific Activity of Key Carbohydrate Metabolizing Enzymes," Afr. J. Tradit. Complement. Altern. Med., 2017, 14(4), Pages 46-53.

In certain embodiments, the baked food product may contain a processed starch, such as Fibrosmart™. As used herein, the term "processed starch" refers to starch treated physically (e.g. by heat), chemically, and/or enzymatically. In certain embodiments, a processed starch can be a "starch derivative" that includes, but is not limited to, (1) starch or starch components that have been isolated from their grain to remove protein and bran and then partly digested with enzymes or partly hydrolyzed by heat and/or acids, e.g. maltodextrins; or (2) starch or starch components that are chemically modified, e.g. etherified or esterified starch, for better emulsification, solubility or digestibility.

Probiotic Constituent

As used herein, the term "probiotic" refers to live microorganisms, such as certain bacteria and yeast, that when ingested by a host, can be beneficial to the health of the host.

As used herein, the term "probiotic spores" refers to highly resistant spores of probiotic bacteria, e.g. gram-positive bacteria, that are dormant structures with no metabolic activity. Bacterial spores form in response to extreme conditions, such as heat, pressure, extreme acid, or alkaline conditions, any of which kill vegetative, live microorganisms or microflora. In certain embodiments, the probiotic spores comprise spores of *Bacillus coagulans*, a lactic acid-producing catalase positive, motile, and Gram-positive facultative anaerobe bacterial species within the genus *Bacillus*.

Exemplary bacterial probiotic species include, but are not limited to, *Bacillus coagulans*, e.g., *Bacillus coagulans* hammer, preferably *Bacillus coagulans* hammer strain Accession No. ATCC 31284, or one or more strains derived from *Bacillus coagulans* hammer strain Accession No. ATCC 31284 (e.g., ATCC Numbers: GBI-20, ATCC Designation Number PTA-6085; GBI-30 or BC30, ATCC Designation Number PTA-6086; and GBI-40, ATCC Designation Number PTA-6087). See, U.S. Pat. No. 6,849,256 B1, granted on Feb. 1, 2005, the content of which is hereby incorporated by reference in its entirety.

In certain embodiments, the probiotic spores comprise GanedenBC30™ (*B. coagulans* GBI-30, 6086). See, U.S. Pat. No. 9,446,111 B2, granted on Sep. 20, 2016, U.S. Pat. No. 6,461,607 B 1, granted on Oct. 8, 2002, and U.S. Pat. No. 9,597,286 B2, granted on Mar. 21, 2017, the contents of which are hereby incorporated by reference in their entirety. GanedenBC30™ is a probiotic formulation that has received United States FDA Generally Regarded as Safe (or GRAS) status for doses up to 93.6 billion CFU per day. For a probiotic to be effective, it must survive the transit through the stomach and reach the intestines alive, where it confers a benefit. Unlike other live probiotic compositions, GanedenBC30™ has been shown to survive the acidic pH encountered during passage through the stomach and, after germination, the spores are able to populate the intestines. See, Harue Honda, et al., "Impact of GanedenBC30 (*Bacillus coagulans* GBI-30, 6086) on population dynamics of the human gut microbiota in a continuous culture fermentation system," International Journal of Probiotics and Prebiotics, 2011, 6(1), Pages 65-72.

When consumed daily, GanedenBC30™ has been shown in multiple studies to have a supportive effect on the digestive system. See, Kathleen F. Benson, et al., "Probiotic metabolites from *Bacillus coagulans* GanedenBC30™ support maturation of antigen-presenting cells in vitro," World J. Gastroenterol., 2012, 18(16), Pages 1875-1883; Gitte S. Jensen, "GanedenBC30™ cell wall and metabolites: anti-inflammatory and immune modulating effects in vitro," BMC Immunol., 2010, 11(15), Pages 1-14; and J. R. Endres, et al., "One-year chronic oral toxicity with combined reproduction toxicity study of a novel probiotic, *Bacillus coagulans*, as a food ingredient," Food and Chemical Toxicology, 2011, 49(5), Pages 1174-1182.

In other examples, the baked food product is a cookie formed from affixing a crème filling between two biscuits. In some examples, such as Example 2 disclosed herein, the crème filing comprises resistant starch, nut butter, vegetable fat, and spores of a probiotic bacterium. Moreover, several examples provided herein comprise peanuts, almonds, and/ or nut butter, which have been shown to have prebiotic benefits. See, Rosa M. Lamuel-Raventos, et al., "Prebiotic nut compounds and human microbiota," Crit. Rev. Food Sci. Nutr., 2017, 57(14), Pages 3154-3163. The crème filing contains no refined sugars, synthetic vitamins, genetically modified organisms (GMOs), artificial sweeteners or artificial preservatives. In some examples, the spores of the probiotic bacterium may comprise the spores of *Bacillus coagulans*.

When ingested, the baked food product or composition described herein promotes the proliferation of probiotic microorganisms in the lower gastrointestinal tract. In certain embodiments, the prebiotic and probiotic formulation within the cookie can improve mood. In certain embodiments, the prebiotic and probiotic formulation within the cookie can stimulate probiotics that can modify the level of neurotransmitters in the central nervous system, such as dopamine, GABA and/or serotonin, to influence positively a subject's mood. In certain embodiments, the prebiotic and probiotic formulation within the cookie can decrease the expression of biomarkers associated with inflammation including, for example, one or more of interleukins 1, 6 and/or 10.

EXAMPLES

Baked Food Compositions, Crème Filing Compositions, and Cookie Configurations

Example 1—Method for Making the Baked Food Composition (e.g., the Biscuit)

A method of making the baked food composition (e.g., the biscuit) for improving gut health is depicted in FIG. 2. The method of FIG. 2 includes numerous process steps. The method of FIG. 2 may begin at a process step 102. The process step 102 is followed by a process step 104 that includes blending dry ingredients with a fat. The dry ingredients may include a polyphenol, a resistant starch, and a prebiotic soluble fiber. The fat may be a vegetable fat. A process step 106 follows the process step 104 and includes mixing in water until glomeration and formation of a dough occurs. The process step 106 may occur via use of a horizontal sigma mixer. Biscuits of appropriate size and form can be cut out of the dough using a cookie cutter or a similar device or apparatus.

A process step 108 follows the process step 106 and includes baking the dough in a direct fire five zone tunnel oven at approximately 350° F. for approximately 7 minutes to produce the baked food composition. An optional process step 110 follows the process step 108. The optional process step 110 includes sandwiching a crème filing between two of the baked food compositions (e.g., two of the biscuits) to produce a cookie. A process step 112 follows the process step 108 or the optional process step 110 (if present) to conclude the method of making the baked food composition (e.g., the biscuit) for improving the gut health of FIG. 2.

Example 2—Method for Making the Crème Filing for Use with the Baked Food Composition (e.g., the Biscuit)

Figure 3:
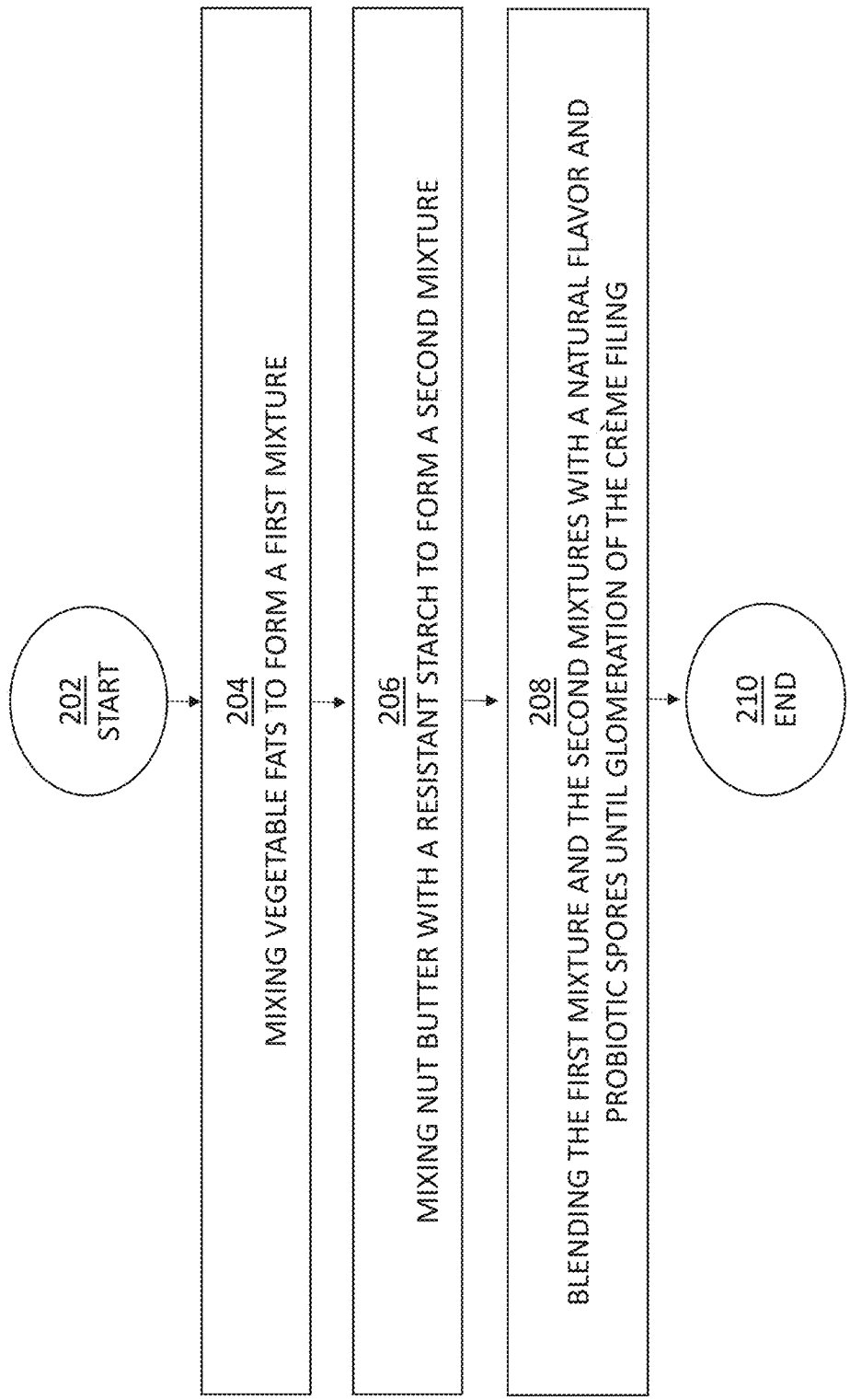
FIG. 3 depicts a block diagram of a method for making a crème filing for use with a biscuit that improves gut health, according to at least some embodiments disclosed herein.

A method of making the crème filing for use with the biscuit that improves gut health is depicted in FIG. 3. The method of FIG. 3 includes numerous process steps. The method of FIG. 3 begins at a process step 202. The process step 202 is followed by a process step 204 that includes mixing vegetable fats to form a first mixture. The process step 204 may occur via use of a Peters machine or a similar machine or apparatus. A process step 206 follows the process step 204 and includes mixing nut butter with a resistant starch to form a second mixture.

A process step 208 follows the process step 206 and includes blending the first mixture and the second mixture with a natural flavor and probiotic spores until glomeration of the crème filing occurs. This may occur for approximately 1 minute. The natural flavor may be vanilla extract, among others not explicitly listed herein. Moreover, in some examples, the probiotic powder may include GanedenBC30™. A process step 210 follows the process step 208 and concludes the method of FIG. 3. The crème filing created by FIG. 3 may be sandwiched between two biscuits (formed from Example 1) to form a cookie.

Example 3—Baked Food Composition

A baked food composition or "base" may include numerous ingredients, as depicted in FIG. 1. According to FIG. 1, the baked food composition or the biscuit may include approximately 0.017 grams of kiwi fruit powder, approximately 15.98 grams of toasted lupin, approximately 1.644 grams of tigernut flour, approximately 4.213 grams of a resistant dextrin, such as Fibersmart™, and approximately 2.677 grams of an IMO. It should be appreciated that in some examples, the IMO is not used or included.

Example 4—Crème Filing Composition

An exemplary composition of the crème filing is also depicted in FIG. 1. According to FIG. 1, the crème filing may include: approximately 2.106 grams of the resistant dextrin, such as Fibersmart™, and 0.075 grams of probiotic powder.

Example 5—Salted Almond Butter Baked Food Composition

A salted almond butter baked food composition may include numerous ingredients, such as: approximately 5.57% of coconut sugar, approximately 2.43% of almond butter, approximately 0.24% peanut butter, approximately 7.75% of palm fruit, approximately 1.94% of faba bean protein, approximately 0.40% of sea salt, approximately 0.97% of sunflower lecithin, approximately 0.44% of vanilla extract, approximately 0.48% of cinnamon, approximately 7.90% of water, approximately of 1.69% of ClearTaste solution, approximately 43.59% of toasted lupin flour, approximately 0.04% of monk fruit, approximately 16.96% of the resistant dextrin, such as tapioca Fibersmart™ powder, approximately 4.85% of almond flour, approximately 3.40% of tigernut flour, approximately 1.28% of hemp seeds, and approximately 0.07% of kiwi fruit powder. The ClearTaste solution may be formed by diluting 100 mg ClearTaste/100 mL water.

The method to make the salted almond butter baked food composition substantially follows the method of making the baked food composition (e.g., the biscuit) for improving gut health of Example 1. However, in this example, the following components are initially mixed for approximately 4 minutes: approximately 5.57% of coconut sugar, approximately 2.43% of almond butter, approximately 0.24% peanut butter, approximately 7.75% of palm fruit, approximately 1.94% of faba bean protein, approximately 0.40% of sea salt, approximately 0.97% of sunflower lecithin, approximately 0.44% of vanilla extract, approximately 0.48% of cinnamon, approximately 7.90% of water, and approximately of 1.69% of ClearTaste solution. Then, the following components are added to the first mixture and are mixed for approximately 1½ minutes: approximately 43.59% of toasted lupin flour, approximately 0.04% of monk fruit, approximately 16.96% of the resistant dextrin, such as tapioca Fibersmart™ powder, approximately 4.85% of almond flour, approximately 3.40% of tigernut flour, approximately 1.28% of hemp seeds, and approximately 0.07% of kiwi fruit powder.

Example 6—Almond Butter Crème Filing Composition

An almond butter vanilla crème filing composition may include numerous ingredients, such as: approximately 31.91% of almond butter, approximately 7.95% of coconut milk powder, approximately 4.86% of palm fruit, approximately 0.64% of sea salt, approximately 0.02% of monk fruit, approximately 23.93% of the resistant dextrin, such as tapioca Fibersmart™ powder, approximately 0.38% of natural vanilla flavor, approximately 29.72% of base meal, and approximately 0.59% of GanedenBC30™ probiotic powder.

It should be appreciated that herein, "base meal" or "meal" refers to the baked food composition that is in a powder form and used to thicken the crème filing composition. As such, the components in the "base" or "food composition" are also found as a percentage of the crème filing formulation.

The method to make the almond butter vanilla crème filing composition of this example substantially follows the method of making the crème filing for use with the biscuit that improves gut health in Example 2. However, in this example, the components of the almond butter vanilla crème filing composition are mixed for approximately 8 minutes.

Example 7—Cookie Formed from Biscuits of Example 5 and Crème Filing Composition of Example 6

The crème filing composition of Example 6 (e.g., the almond butter vanilla crème filing composition) may be sandwiched between two biscuits of Example 5 (e.g., the salted almond butter baked food composition) to produce a cookie. The biscuits (e.g., the salted almond butter baked food composition) may comprise approximately 67% to approximately 72% by weight of the cookie and the crème filing composition (e.g., the almond butter vanilla crème filing composition) may comprise approximately 28% to approximately 33% by weight of the cookie. In a preferred embodiment, the biscuits (e.g., the salted almond butter baked food composition) may comprise approximately 67% by weight of the cookie and the crème filing composition (e.g., the almond butter vanilla crème filing composition) may comprise approximately 33% by weight of the cookie.

Example 8—Salted Peanut Butter Chocolate Coconut Baked Food Composition

A salted peanut butter chocolate coconut baked food composition may include numerous ingredients, such as: approximately 5.58% of coconut sugar, approximately 0.24% of almond butter, approximately 3.15% of peanut butter, approximately 7.27% of palm fruit, approximately 1.94% of faba bean protein, approximately 0.39% of sea salt, approximately 0.97% of sunflower lecithin, approximately 0.61% of vanilla extract, approximately 0.30% of peanut flavor, approximately 0.48% of cinnamon, approximately 8.48% of water, approximately 1.70% of ClearTaste solution, approximately 41.08% of toasted lupin flour, approximately 0.04% of monk fruit, approximately 16.97% of the resistant dextrin, such as tapioca Fibersmart™ powder, approximately 6.06% of peanut flour, approximately 3.39% of tigernut flour, approximately 1.28% of desiccated coconut medium, and approximately 0.07% of kiwi fruit powder. The ClearTaste solution may be formed by diluting 100 mg ClearTaste/100 mL water.

The method to make the salted peanut butter chocolate coconut baked food composition of this example substantially follows the method of making the baked food composition (e.g., the biscuit) for improving gut health of Example 1. However, in this example, the following components are initially mixed for approximately 4 minutes:

approximately 5.58% of coconut sugar, approximately 0.24% of almond butter, approximately 3.15% of peanut butter, approximately 7.27% of palm fruit, approximately 1.94% of faba bean protein, approximately 0.39% of sea salt, approximately 0.97% of sunflower lecithin, approximately 0.61% of vanilla extract, approximately 0.30% of peanut flavor, approximately 0.48% of cinnamon, approximately 8.48% of water, and approximately 1.70% of ClearTaste solution. Then, the following components are added to the first mixture and are mixed for approximately 2½ minutes: approximately 41.08% of toasted lupin flour, approximately 0.04% of monk fruit, approximately 16.97% of the resistant dextrin, such as tapioca Fibersmart™ powder, approximately 6.06% of peanut flour, approximately 3.39% of tigernut flour, approximately 1.28% of desiccated coconut medium, and approximately 0.07% of kiwi fruit powder.

Example 9—Salted Peanut Butter Crème Filing Composition

A salted peanut butter chocolate coconut crème filing composition may include numerous ingredients, such as: approximately 31.92% of peanut butter, approximately 7.98% of coconut milk powder, approximately 5.11% of palm fruit, approximately 0.67% of sea salt, approximately 7.77% of cocoa powder, approximately 0.02% of monk fruit, approximately 23.94% of the resistant dextrin, such as tapioca Fibersmart™ powder, approximately 0.53% of vanilla extract, approximately 0.20% of cocoa butter extract, approximately 21.27% of base meal, and approximately 0.59% of GanedenBC30™ probiotic powder.

The method to make the salted peanut butter chocolate coconut crème filing composition of this example substantially follows the method of making the crème filing for use with the biscuit that improves gut health in Example 2. However, in this example, the components of the crème filing composition are mixed for approximately 8 minutes.

Example 10—Cookie Formed from Biscuits of Example 8 and Crème Filing Composition of Example 9

The crème filing composition of Example 9 (e.g., the salted peanut butter chocolate coconut crème filing composition) may be sandwiched between two biscuits of Example 8 (e.g., the salted peanut butter chocolate coconut baked food composition) to produce a cookie. The biscuits (e.g., the salted peanut butter chocolate coconut baked food composition) may comprise approximately 67% to approximately 72% by weight of the cookie and the crème filing composition (e.g., the salted peanut butter chocolate coconut crème filing composition) may comprise approximately 28% to approximately 33% by weight of the cookie. In a preferred embodiment, the biscuits may comprise approximately 67% by weight of the cookie and the crème filing composition may comprise approximately 33% by weight of the cookie.

Example 11—Sunflower Butter Vanilla Chai Baked Food Composition

A sunflower butter vanilla chai baked food composition may include numerous ingredients, such as: approximately 5.56% of coconut sugar, approximately 2.90% of sunflower butter, approximately 8.22% of palm fruit, approximately 1.93% of faba bean protein, approximately 0.56% of sea salt, approximately 0.97% of sunflower lecithin, approximately 0.60% of vanilla extract, approximately 0.48% of cinnamon, approximately 8.22% of water, approximately 1.69% of ClearTaste solution, approximately 41.11% of toasted lupin flour, approximately 0.03% of monk fruit, approximately 16.93% of the resistant dextrin, such as tapioca Fibersmart™ powder, approximately 6.05% of coconut flour, approximately 3.39% of tigernut flour, approximately 1.28% of black chai seeds, and approximately 0.07% of kiwi fruit powder. The ClearTaste solution may be formed by diluting 100 mg ClearTaste/100 mL water.

The method to make the sunflower butter vanilla chai baked food composition of this example substantially follows the method of making the baked food composition (e.g., the biscuit) for improving gut health of Example 1. However, in this example, the following components are first mixed for approximately 4 minutes: approximately 5.56% of coconut sugar, approximately 2.90% of sunflower butter, approximately 8.22% of palm fruit, approximately 1.93% of faba bean protein, approximately 0.56% of sea salt, approximately 0.97% of sunflower lecithin, approximately 0.60% of vanilla extract, approximately 0.48% of cinnamon, approximately 8.22% of water, and approximately 1.69% of ClearTaste solution. Then, the following components are added to the first mixture and are mixed for approximately 2½ minutes: approximately 41.11% of toasted lupin flour, approximately 0.03% of monk fruit, approximately 16.93% of the resistant dextrin, such as tapioca Fibersmart™ powder, approximately 6.05% of coconut flour, approximately 3.39% of tigernut flour, approximately 1.28% of black chai seeds, and approximately 0.07% of kiwi fruit powder.

Example 12—Sunflower Butter Vanilla Chai Crème Filing Composition

A sunflower butter vanilla chai crème filing composition may include numerous ingredients, such as: approximately 31.56% of sunflower butter, approximately 7.86% of coconut milk powder, approximately 4.81% of palm fruit, approximately 1.05% of sea salt, approximately 0.02% of monk fruit, approximately 23.68% of the resistant dextrin, such as tapioca Fibersmart™ powder, approximately 1.05% of vanilla extract, approximately 29.39% of base meal, and approximately 0.58% of GanedenBC30™ probiotic powder.

The method to make the sunflower butter vanilla chai crème filing composition of this example substantially follows the method of making the crème filing for use with the biscuit that improves gut health in Example 2. However, in this example, the components of the crème filing are mixed for approximately 8 minutes.

Example 13—Cookie Formed from Biscuits of Example 11 and Crème Filing Composition of Example 12

The crème filing composition of Example 12 (e.g., the sunflower butter vanilla chai crème filing composition) may be sandwiched between two biscuits of Example 11 (e.g., the sunflower butter vanilla chai baked food composition) to produce a cookie. The biscuits may comprise approximately 67% to approximately 72% by weight of the cookie and the crème filing composition may comprise approximately 28% to approximately 33% by weight of the cookie. In a preferred embodiment, the biscuits may comprise approximately 67% by weight of the cookie and the crème filing composition may comprise approximately 33% by weight of the cookie.

Methodologies

Ex-Vivo Fermentation Study

The prebiotic effect of the baked food composition or the biscuit on human gut microbiota was investigated ex vivo in a model of the human colon mimicking physiological and microbiological conditions of a large intestine. See, Christopher Le Lay, et al., "On Lactococcus lactis UL719 Competitivity and Nisin (Nisaplin(®)) Capacity to Inhibit Clostridium Difficile in a Model of Human Colon," Front Microbiol., 2015, 6, Page 1020. Feces from two healthy adult volunteers were freshly collected and within 1 hour, used to inoculate gellan (2.5%, w/v) and xanthan (0.25%, w/v) beads under anaerobic conditions. See, Gwenaeelle Le Blay, et al., "Stability and Inhibitory Activity of Pediocin PA-1 Against Listeria sp. in Simulated Physiological Conditions of the Human Terminal Ileum.," Probiotics and Antimicrobial Proteins, 2012, 4, Pages 250-258.

Gel beads (30%) were then transferred into a stirred glass reactor containing fresh Macfarlane culture medium. Fermentation simulating physiological and microbiological conditions of human intestine are described in Christopher Le Lay, et al., "On Lactococcus lactis UL719 Competitivity and Nisin (Nisaplin(®)) Capacity to Inhibit Clostridium Difficile in a Model of Human Colon," Front Microbiol., 2015, 6, Page 1020 and Gwenaeelle Le Blay, et al., "Stability and Inhibitory Activity of Pediocin PA-1 Against Listeria sp. in Simulated Physiological Conditions of the Human Terminal Ileum.," Probiotics and Antimicrobial Proteins, 2012, 4, Pages 250-258, the contents of which are hereby incorporated by reference in their entireties.

Solubilized active ingredients may be described in Example 4 and may be depicted in FIG. 1. The solubilized active ingredients or components for the baked food composition or the biscuit may include approximately 0.017 grams of kiwi fruit powder, approximately 15.98 grams of toasted lupin, approximately 1.644 grams of tigernut flour, approximately 4.213 grams of the resistant dextrin, such as Fibersmart™, and approximately 2.677 grams of the IMO (e.g., VitaFiber™).

These solubilized active ingredients or components for the baked food composition were added daily to the simulated colon at approximately 3.56 g/0.1 L, calculated for an estimated daily intake of approximately 26.7 grams of active ingredients/day (e.g., an approximately 40 grams of the cookie serving), accounting for the reactor volume of approximately 0.1 L compared to approximately 0.75 L for the proximal colon volume, and a chime medium supply of approximately 0.2 L medium per day, giving a mean retention time of approximately 12.5 hours. Microcrystalline cellulose was used a control. Samples were collected from the bioreactor at numerous time periods, including: 0, 4, 8, 16, 24, 36 and 48 hours.

Genomic Analysis

Microbiota levels (specific primers for Bacillus coagulans and Faecalibacterium prausnitzii to study the stimulating effect of the baked food formulation of FIG. 1) were quantified using quantitative polymerase chain reaction (or qPCR), which refers to a laboratory technique of molecular biology based on the polymerase chain reaction (PCR). Further, qPCR is a collection of methods for estimating a quantity of copies of a specific DNA template in a sample. See, Christopher Le Lay, et al., "On Lactococcus lactis UL719 Competitivity and Nisin (Nisaplin(®)) Capacity to Inhibit Clostridium difficile in a Model of Human Colon," Front Microbiol., 2015, 6, Page 1020.

It should be appreciated that "16S rNA" refers to a ribosomal RNA that is a component of the prokaryotic ribosome 30S subunit. The "S" in 16S is a sedimentation coefficient, that is, an index reflecting the downward velocity of the macromolecule in the centrifugal field. The higher the value, the greater the molecule. The 16S rRNA gene is the DNA sequence corresponding to rRNA encoding bacteria, which exists in the genome of all bacteria. 16S rRNA is highly conserved and specific, and the gene sequence is long enough. The 16S rRNA gene is approximately 1600 base pairs long and includes nine hypervariable regions of varying conservation (V1-V9). See, Yu S. Bukin, et al., "The effect of 16S rRNA region choice on bacterial community metabarcoding results," Nature: Scientific Data, 2019, 6; M. Kim, et al., "Evaluation of different partial 16S rRNA gene sequence regions for phylogenetic analysis of microbiomes," Journal of Microbiological Methods, 2011, 84, Pages 81-87; Y. Wang, et al., "Conservative fragments in bacterial 16S rRNA genes and primer design for 16S ribosomal DNA amplicons in metagenomic studies," PloS ONE, 2009, 4, Page e7401; and S. G. Tringe, et al., "A renaissance for the pioneering 16S rRNA gene," Current Opinion in Microbiology, 2008, 11, Pages 442-446. Further, the 16S rRNA is a ribosomal RNA necessary for the synthesis of all prokaryotic proteins. Each bacterium contains 5~10 copies of 16S rRNA, which makes the detection sensitivity highly.

16S ribosomal RNA sequences have been used extensively in the classification and identification of bacteria and archaea. The comparison of almost complete 16S rRNA gene sequences has been widely used to establish taxonomic relationships between prokaryotic strains, with 98.65% similarity currently recognized as the cutoff for delineating species. The comparison of the 16S rRNA gene sequence of an isolate against sequences of type strains of all prokaryotic species provides an accurate and convenient way to routinely classify and identify prokaryotes. See, Mincheol Kim, et al., "Chapter 4-16S rRNA Gene-Based Identification of Bacteria and Archaea using the EzTaxon Server," Methods in Microbiology, 2014, 41, Pages 61-74.

Additionally, more conservative regions of 16S rNA are useful for determining the higher-ranking taxa, whereas more quickly evolving ones can help identify genus or species. Use of the full V3-V4 regions of 16S rRNA has been shown to contribute to a more in-depth characterization of the microbial composition. See, Rodrigo Garcia-Lopez, et al., "Doing More with Less: A Comparison of 16S Hypervariable Regions in Search of Defining the Shrimp Microbiota," Microorganisms, 2020, 8(134), Pages 1-28. As such, the bacterial diversity was experimentally determined by sequencing the V3-V4 region of 16S rNA using the MiSeq System.

Metabolomic Analysis

Humans lack the enzymes to degrade the bulk of dietary fibers. Therefore, these nondigestible carbohydrates pass the upper gastrointestinal tract unaffected and are fermented in the cecum and the large intestine by the anaerobic cecal and colonic microbiota. Fermentation results in multiple groups of metabolites, of which short-chain fatty acids (SCFAs) are the major group. See, J. K. Nicholson, et al., "Host-gut microbiota metabolic interactions," Science, 2012, 336 (6086), Pages 1262-1267; and C. C. Roy, et al., "Short-chain fatty acids: ready for prime time?," Nutr. Clin. Pract., 2006, 21(4), Pages 351-366.

SCFAs are a necessary waste product, required to balance redox equivalent production in the anaerobic environment of the gut. See, Milan J. A. van Hoek, et al., "Redox balance is key to explaining full vs. partial switching to low-yield metabolism," BMC Syst. Biol., 2012, 6(22). SCFAs are saturated aliphatic organic acids that consist of one to six carbons of which acetate, propionate, and butyrate are the most abundant (≥95%). See, S. I. Cook, et al., "Review article: short chain fatty acids in health and disease," Aliment Pharmacol. Ther., 1998, 12(6), Pages 499-507. Acetate, propionate, and butyrate are present in an approximate molar ratio of 60:20:20 in the colon and stool. See, E. Hijova, et al., "Short chain fatty acids and colonic health," Bratisl Lek Listy., 2007, 108(8), Pages 354-358; and J. H. Cummings, et al., "Short Chain Fatty Acids in Human Large Intestine, Portal, Hepatic and Venous Blood," Gut, 1987, 28(10), Pages 1221-1227. Depending on the diet, the total concentration of SCFAs decreases from 70 to 140 mM in the proximal colon to 20 to 70 mM in the distal colon. See, D. L. Topping, et al., "Short-chain fatty acids and human colonic function: roles of resistant starch and nonstarch polysaccharides," Physiol. Rev., 2001, 81(3), Pages 1031-1064.

SCFAs have been the subject of much research over the past few decades, as SCFAs play a vital role in maintenance of colonic integrity and metabolism. SCFAs are produced when dietary fiber is fermented by colonic bacteria and are absorbed in the colon, at the same time as sodium and water absorption and bicarbonate secretion. Once absorbed, SCFAs are used preferentially as fuel for colonic epithelial cells and have trophic effects on the epithelium.

Concentrations of short-chain fatty acids were determined using gas chromatography with flame ionization detector (or "GC-FID") and expressed in mM. GC-FID is a common analytical technique that is widely used in the petrochemical, pharmaceutical and natural gas markets. An FID typically uses a hydrogen/air flame into which the sample is passed to oxidize organic molecules and produce electrically charged particles (ions). The ions are collected and produce an electrical signal, which is then measured. As common with other GC techniques, a carrier gas is required with low water and oxygen impurities, since water and oxygen can interact with the stationary phase and cause significant problems, such as high baseline noise and column bleed in the output gas chromatogram, which both reduces the analyzer sensitivity and decreases column lifetime.

Also, amino acids metabolism and production of neuroactive compounds (e.g., GABA, serotonin, and dopamine) by gut microbiota were quantified using gas chromatography-mass spectrometry (or "GC-MS"). It should be appreciated that GC-MS is an analytical method that combines the features of gas-chromatography and mass spectrometry to identify different substances within a test sample. Applications of GC-MS include drug detection, fire investigation, environmental analysis, explosives investigation, and identification of unknown samples.

Results of Methodologies

"Metagenomics" is the study of genetic material recovered directly from environmental samples. This field may also be referred to as environmental genomics, ecogenomics or community genomics. While traditional microbiology, microbial genome sequencing, and genomics rely upon cultivated clonal cultures, early environmental gene sequencing cloned specific genes (often the 16S rRNA gene) to produce a profile of diversity in a natural sample. Such work revealed that the vast majority of microbial biodiversity had been missed by cultivation-based methods. Because of its ability to reveal the previously hidden diversity of microscopic life, metagenomics offers a way to view the microbial world. See, John C. Wooley, et al., "Metagenomics: Facts and Artifacts, and Computational Challenges," J. Comput. Sci. Technol., 2009, 25(1), Pages 71-81.

Metagenomic results are depicted, at least, in FIG. 4A, FIG. 4B, FIG. 4C, FIG. 5, FIG. 6, FIG. 7A-FIG. 7J, and FIG. 8A-FIG. 8C.

Example 14—Rarefaction Curves

Rarefaction is a statistical technique used to approximate the number of operational taxonomic units (OTUs) expected in a random sample of individuals taken from a sample collection. Rarefaction can be used to measure bacterial richness (e.g., relative richness; measurement of OTUs actually observed in samples). See, Bo-Ra Kim, et al., "Deciphering Diversity Indices for a Better Understanding of Microbial Communities," J. Microbiol. Biotechnol., 2017, 27(12), Pages 2089-2093.

The diversity index is a quantitative measure that reflects how many different types (such as species) there are in a dataset (a community) and that can simultaneously take into account the phylogenetic relations among the individuals distributed among those types, such as richness, divergence or evenness. It should be appreciated that the analysis of microbial community diversity, there is no general agreement on which diversity index is the best to use. See, J. B. Hughes, et al., "Application of ecological diversity statistics in microbial ecology," Molecular Microbial. Ecology Manual, 2004, Second Edition, 7.01, Pages 1321-1344.

Chao1 indices are used to estimate richness. See, Bo-Ra Kim, et al. More specifically, Chao1 is a nonparametric method for estimating the number of species in a community. The Chao richness estimator is based on the concept that rare species infer the most information about the number of missing species. See, A. Chao, "Non-parametric estimation of the number of classes in a population," Journal of Statistics, 1984, 11, Pages 265-270; and A. Chao, "Estimating the Population Size for Capture-Recapture Data with Unequal Catchability," Biometrics, 1987, 43, Pages 783-791.

Shannon-Weaver and Simpson diversity indices are commonly used in bacterial diversity measurement based on OTUs. The OTUs are inferred to exist based on sequence data, and can be defined at different levels of resolution (e.g., phylum, class, order, family, genus, and species). See, Bo-Ra Kim, et al. Specifically, the Shannon diversity index is another index that is commonly used to characterize species diversity in a community. The Shannon index accounts for both abundance and evenness of the species present.

Figure 4A:
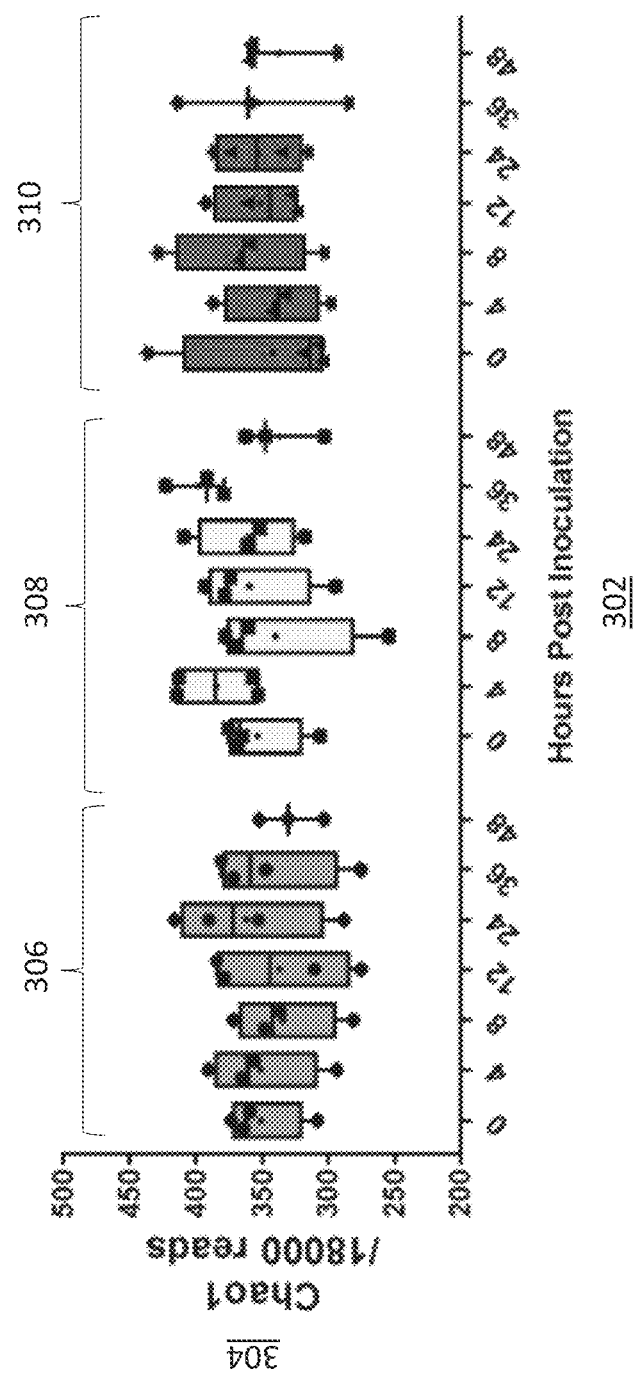
FIG. 4A depicts a graphical representation of a rarefaction curve at multiple sequence depths based on a Chao 1 value, according to at least some embodiments disclosed herein.
Figure 4B:
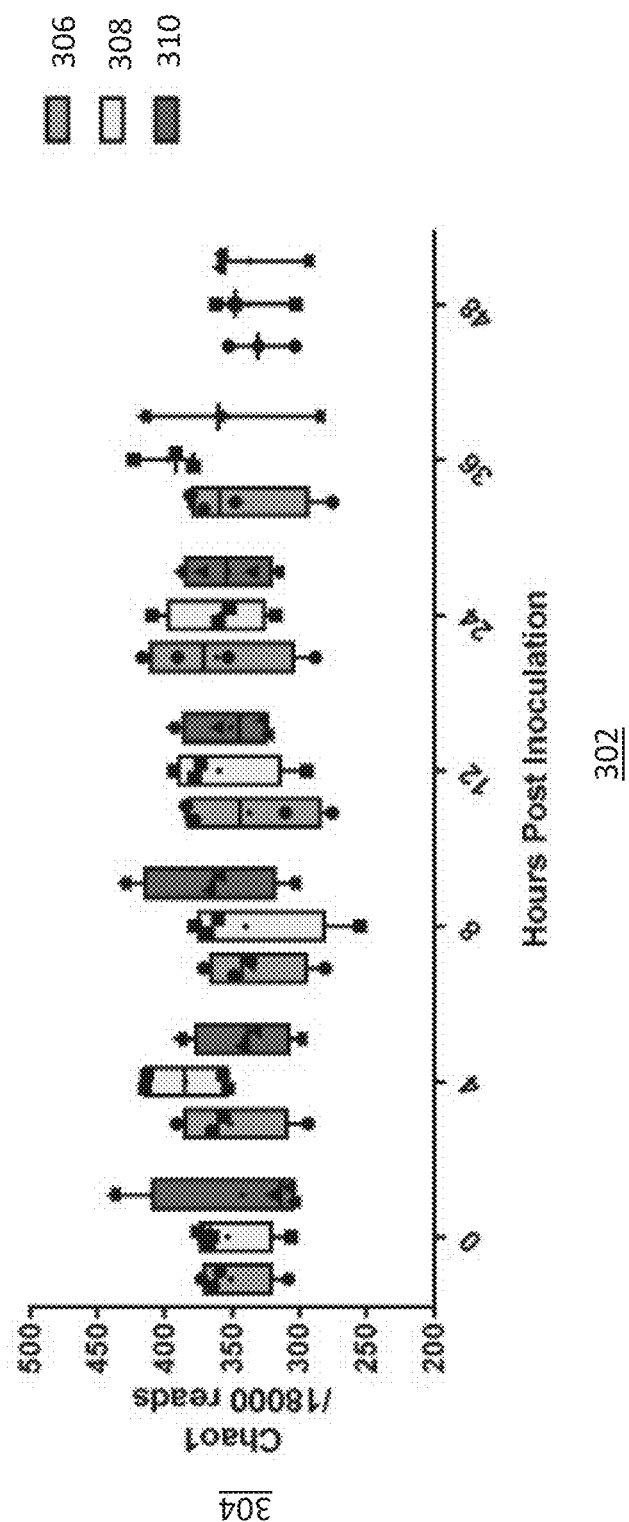
FIG. 4B depicts another graphical representation of a rarefaction curve at multiple sequence depths based on a Chao 1 value, according to at least some embodiments disclosed herein.
Figure 4C:
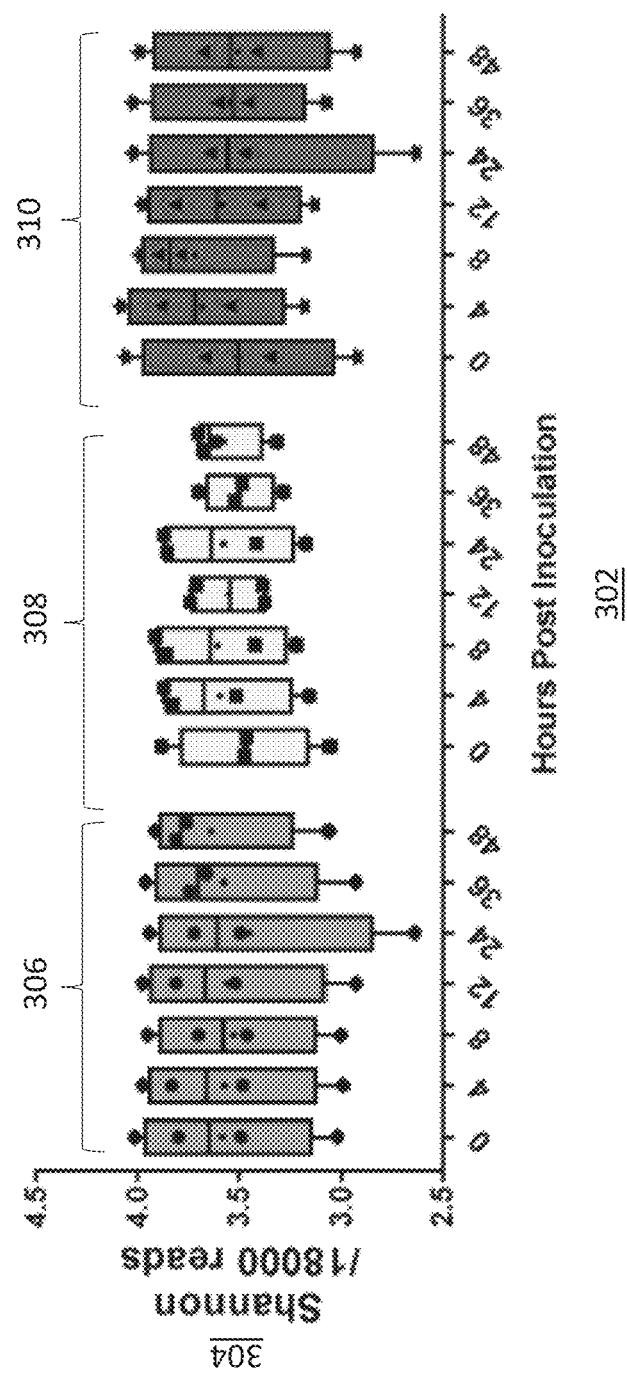
FIG. 4C depicts another graphical representation of a rarefaction curve at multiple sequence depths based on a Shannon value, according to at least some embodiments disclosed herein.

FIG. 4A, FIG. 4B, and FIG. 4C depict graphical representations of rarefaction curves at multiple sequence depths based on diversity indices. Specifically, FIG. 4A and FIG. 4B depict a control 306, fibers 308 of FIG. 1, and microcrystalline (or MC) cellulose 310 on a graph having a quantity of hours post-inoculation 302 on an x-axis and a diversity index (e.g., the Chao1 index) 304 on the y-axis. FIG. 4C depicts the control 306, the fibers 308 of FIG. 1, and the MC cellulose 310 on the graph having the quantity of hours post-inoculation 302 on the x-axis and another diversity index (e.g., the on Shannon index) 304 the y-axis.

Example 15—Taxonomic Cladogram

Linear discriminant analysis (LDA), normal discriminant analysis (NDA), or discriminant function analysis is a generalization of Fisher's linear discriminant, a method used in statistics, pattern recognition, and machine learning to find a linear combination of features that characterizes or separates two or more classes of objects or events.

Linear discriminant analysis effect size or "LEfSe" determines the features (e.g., organisms, clades, operational taxonomic units, genes, or functions) most likely to explain differences between classes by coupling standard tests for statistical significance with additional tests encoding biological consistency and effect relevance. Class comparison methods typically predict biomarkers consisting of features that violate a null hypothesis of no difference between classes.

Further, LEfSe emphasizes statistical significance, biological consistency, and effect relevance, allowing researchers to identify differentially abundant features that are also consistent with biologically meaningful categories. LEfSe first robustly identifies features that are statistically different among biological classes. LEfSe then performs additional tests to assess whether these differences are consistent with respect to expected biological behavior; for example, given some known population structure within a set of input samples, is a feature more abundant in all population subclasses or in just one? As a last step, LEfSe uses LDA to estimate the effect size of each differentially abundant feature and, if desired by the investigator, to perform dimension reduction. See, Nicola Segata, et al., "Metagenomic biomarker discovery and explanation," Genome Biol., 2011, 12(R60), Pages 1-18. The visualization of the discovered biomarkers on taxonomic trees provides an effective means for summarizing the results in a biologically meaningful way.

A "cladogram" is a diagram that may be used to show relations among organisms. A cladogram uses lines that branch off in different directions ending at a clade, a group of organisms with a last common ancestor. There are many shapes of cladograms, but they all have lines that branch off from other lines. The lines can be traced back to where they branch off. These branching off points represent a hypothetical ancestor (not an actual entity), which can be inferred to exhibit the traits shared among the terminal taxa above it. This hypothetical ancestor might then provide clues about the order of evolution of various features, adaptation, and other evolutionary narratives about ancestors.

Figure 5:
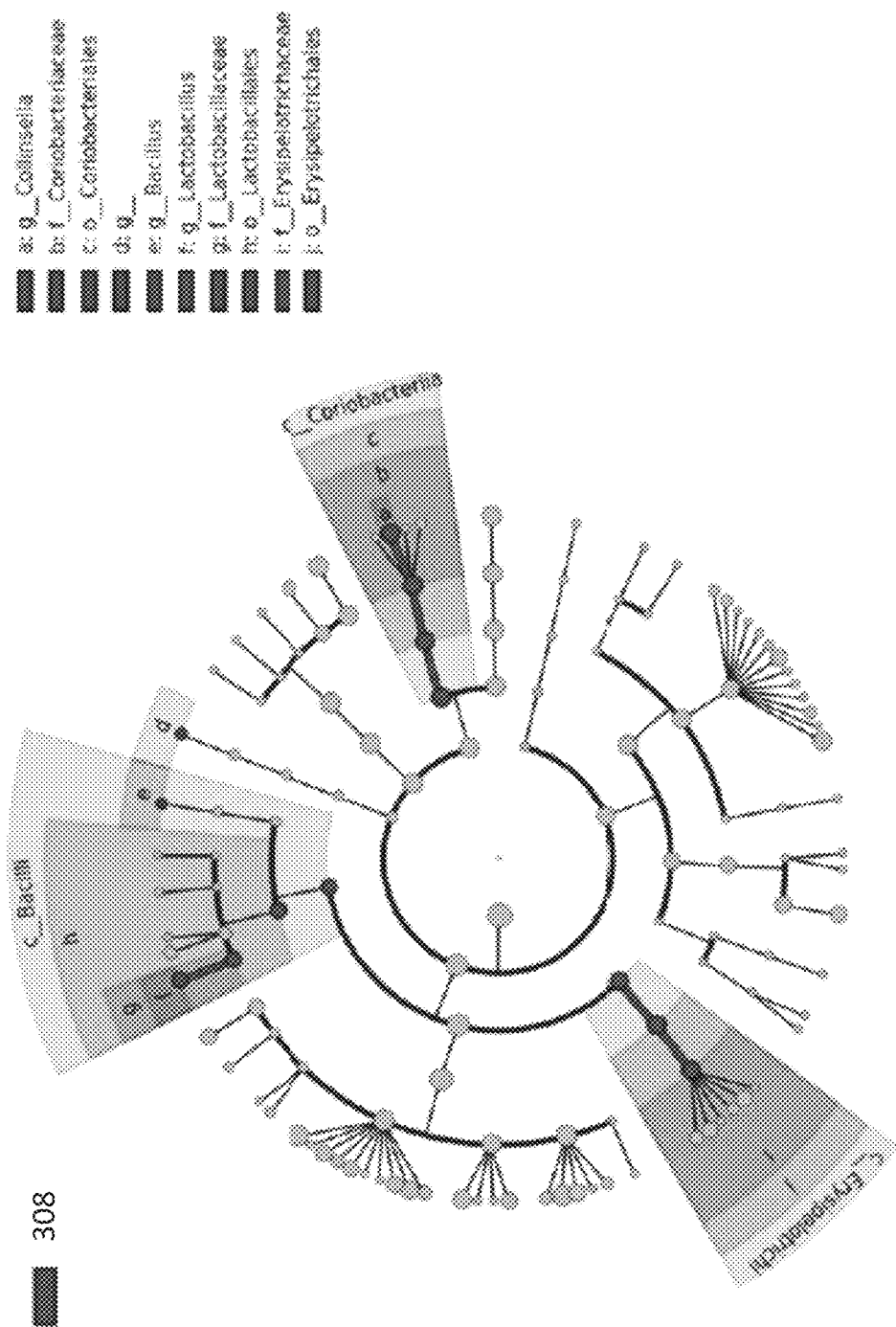
FIG. 5 depicts a taxonomic cladogram obtained from a linear discriminant analysis effect size (LEfSe) analysis of 16S sequences with a relative abundance ≥0.5%, according to at least some embodiments disclosed herein.

Differential taxa between the control 306 and the fibers 308 of FIG. 1 are depicted in a taxonomic cladogram in FIG. 5. More specifically, FIG. 5 depicts the following: *collinsella* (a genus of Actinobacteria, in the family Coriobacteriaceae), coriobacteriaceae (a family of Actinobacteria), coriobacteriales (a family of Actinobacteria), *bacillus* (which is a genus of Gram-positive, rod-shaped bacteria, a member of the phylum Firmicutes), *lactobacillus* (which is a genus of Gram-positive, facultative anaerobic or microaerophilic, rod-shaped, non-spore-forming bacteria), lactobacillaceae (which is a family of lactic acid bacteria), lactobacillales (which is lactic acid bacteria (LAB) and is an order of Gram-positive bacteria that are either rod-or coccus-shaped), erysipelotrichaceae (which is a class of bacteria of the phylum Firmicutes), and erysipelotrichales (a class of bacteria of the phylum Firmicutes).

The taxonomic cladogram was obtained from LEfSe analysis of 16S sequences having a relative abundance of ≥0.5%. Moreover, the brightness of each dot in FIG. 5 is proportional to its effect size. Fiber-enriched taxa are also depicted in FIG. 5 with a positive LDA score in black.

Example 16—Graphical Representation of Taxa from FIG. 5

Figure 6:
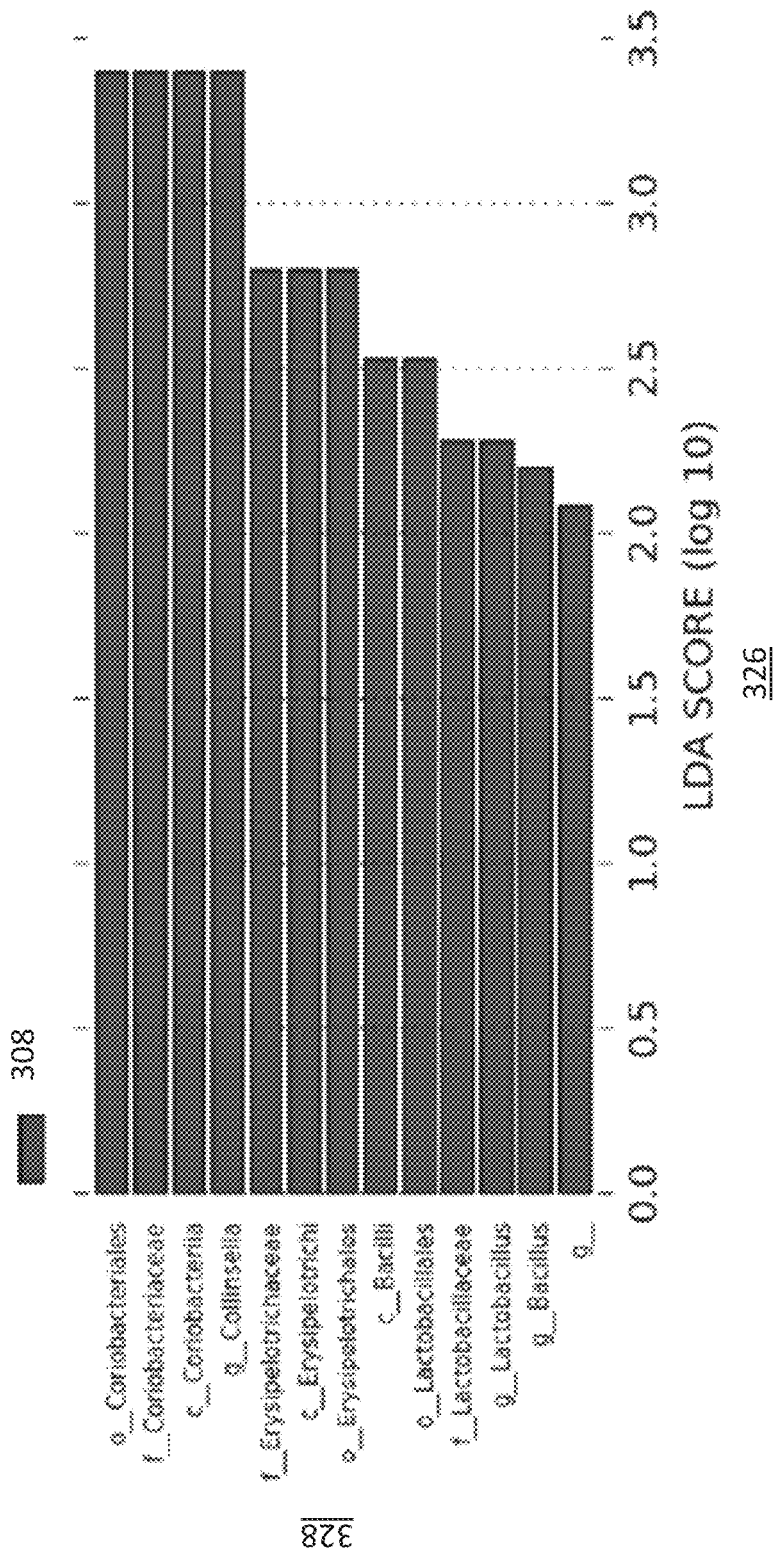
FIG. 6 depicts a graphical representation of taxa from FIG. 5 meeting a linear discriminant analysis (LDA) significant threshold >2, according to at least some embodiments disclosed herein.

A graphical representation of the taxa from FIG. 5 meeting an LDA significant threshold >2 are depicted in FIG. 6.

As can be seen in FIG. 6, coriobacteriales, coriobacteriaceae, and coriobacteriia have an LDA score of approximately 3.4. Erysipelotrichaceae, erysipelotrichi, and erysipelotrichales have the LDA score of approimxately 2.7. Bacilli and lactobacillales have the LDA score of approximately 2.5. Lactobacillaceae and *lactobacillus* have the LDA score of approximately 2.3. *Bacillus* has the LDA score of approximately 2.1.

Example 17—Relative Abundance of Differential Taxa Between the Control 306 and the Fibers 308 of FIG. 1

FIG. 7A-FIG. 7J depict graphical representations of differential taxa between the control 306 and the fibers 308 of FIG. 1. More specifically, FIG. 7A-FIG. 7J depict the relative abundance of differential taxa between the control 306 and the fibers 308 of FIG. 1. The relative abundance is the abundance of a species (by any measure), divided by the total abundance of all species combined. Such relative abundance 330 is measured on the y-axis in FIG. 7A-FIG. 7J.

The increase observed in the genus *Bacillus* in FIG. 5, FIG. 6, FIG. 7E, and FIG. 7F is expected and attributable to the probiotic powder of FIG. 1. Such results were confirmed by FIG. 9 herein. Furthermore, the genus *Lactobacillus* significantly increased after addition of probiotic powder of FIG. 1, as can be seen in FIG. 5, FIG. 6, FIG. 7E, and FIG. 7F, confirming the prebiotic effect of the formulation.

*Collinsella aerofaciens* has been associated with a low risk of colon cancer, and patients with IBD present lower gut levels of this genus than do control individuals. See, Evelyne M. Dewulf, et al., "Insight Into the Prebiotic Concept: Lessons From an Exploratory, Double Blind Intervention Study With Inulin-Type Fructans in Obese Women," Gut, 2013, 62, Pages 1112-1121. The authors reported an association of increased levels of *Collinsella* and Hippurate, a gut-derived metabolite commonly associated with a "healthy phenotype." Hippurate is one of the main discriminant metabolites explaining the difference in urine metabolic profiles between lean and obese or diabetic individuals. A patent application has been filled for the use of *Collinsella aerofaciens* for reducing bloating. See, WO 2010/125472 A1, published on Nov. 4, 2010. Moreover, increased levels of *Collinsella*, a genus belonging to Actinobacteria, was significantly augmented with the probiotic powder of FIG. 1 (as shown in FIG. 5, FIG. 6, FIG. 7H, FIG. 7I, and FIG. 7J).

A previous study investigating altered microbiota composition in patients with major depression disorder (MDD) have reported that relative proportion of Erysipelotrichaceae was significantly lower levels in the MDD than in the healthy control group. See, Haiyin Jiang, et al., "Altered fecal microbiota composition in patients with major depressive disorder," Brain, Behavior, and Immunity, 2015, 48, Pages 186-194. Still, Erysipelotrichaceae is less studied and no clear conclusion has been drawn about a potent role of this family (as opposed to *F. prausnitzii*). Similarly, the Erysipelotrichaceae family has significantly increased after addition of the probiotic powder of FIG. 1 (as shown in FIG. 5, FIG. 6, FIG. 7A, and FIG. 7B).

Figures 7A, 7B:
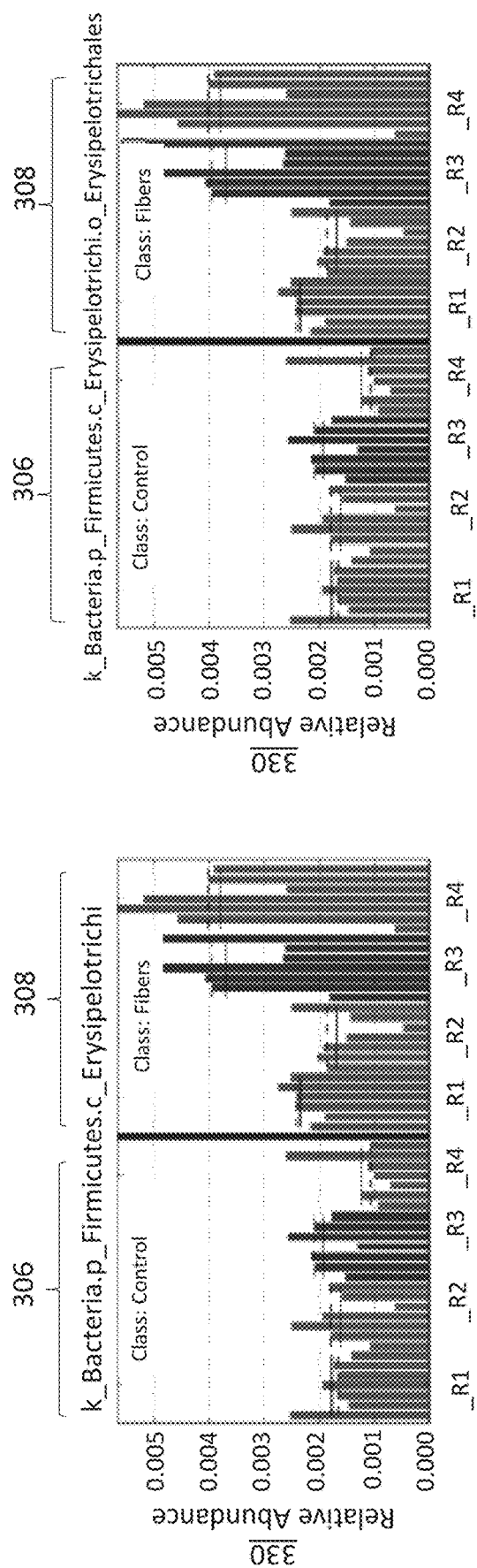
FIG. 7A-FIG. 7J depict graphical representations of differential taxa between a control and fibers of FIG. 1, according to at least some embodiments disclosed herein.
Figures 7C, 7D:
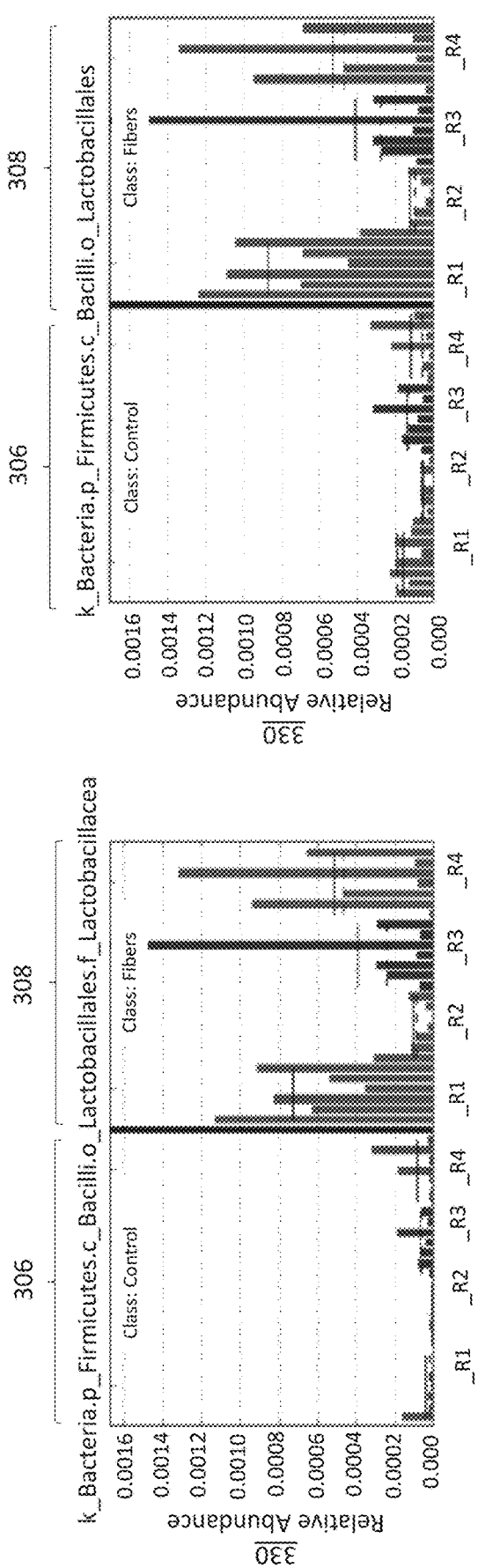
Figure 7E:
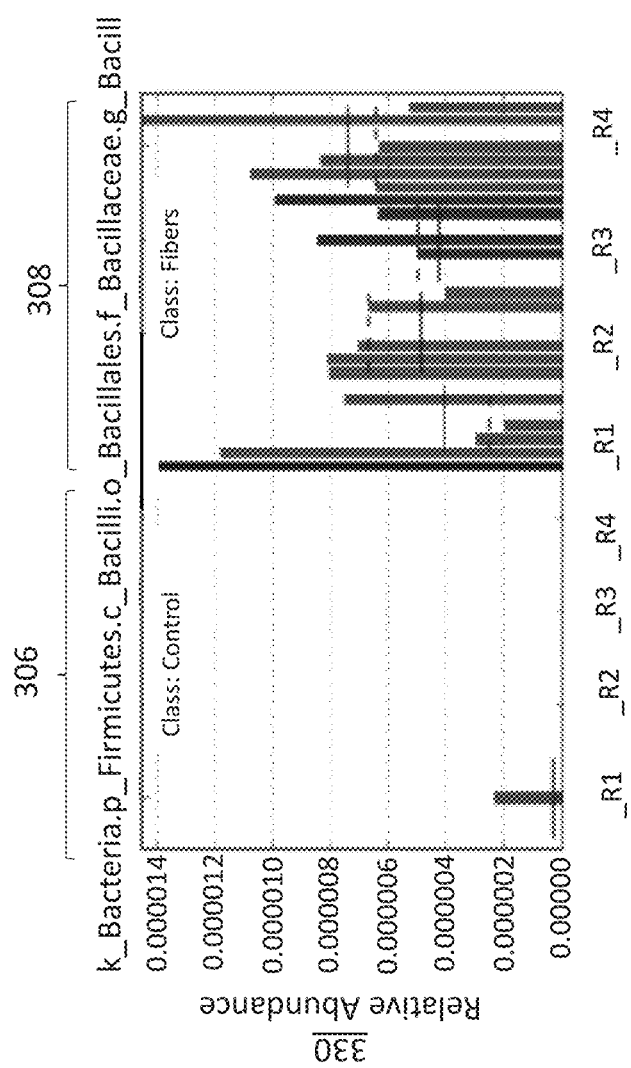
Figure 7F:
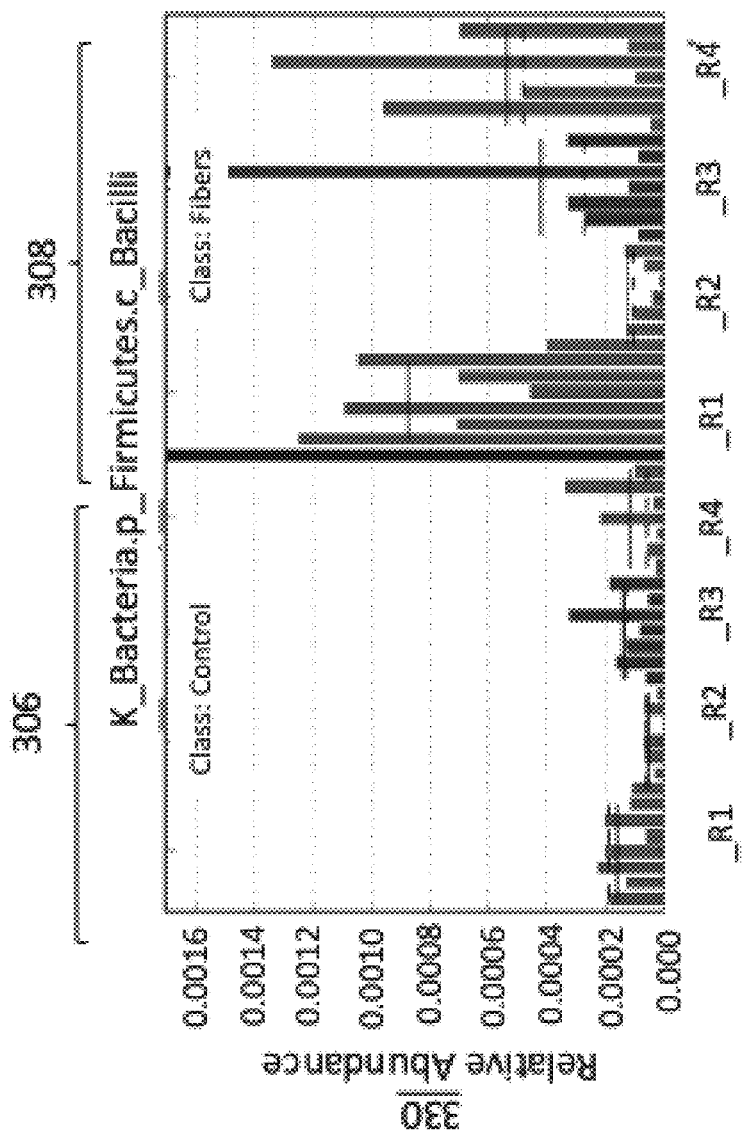
Figure 7G:
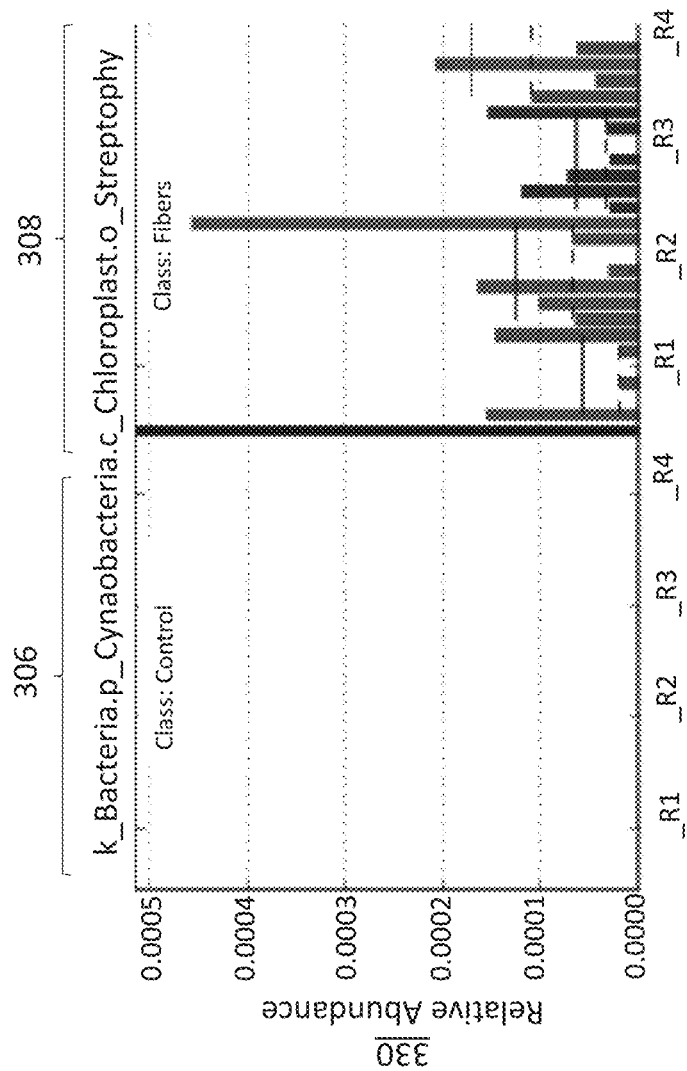
Figure 7H:
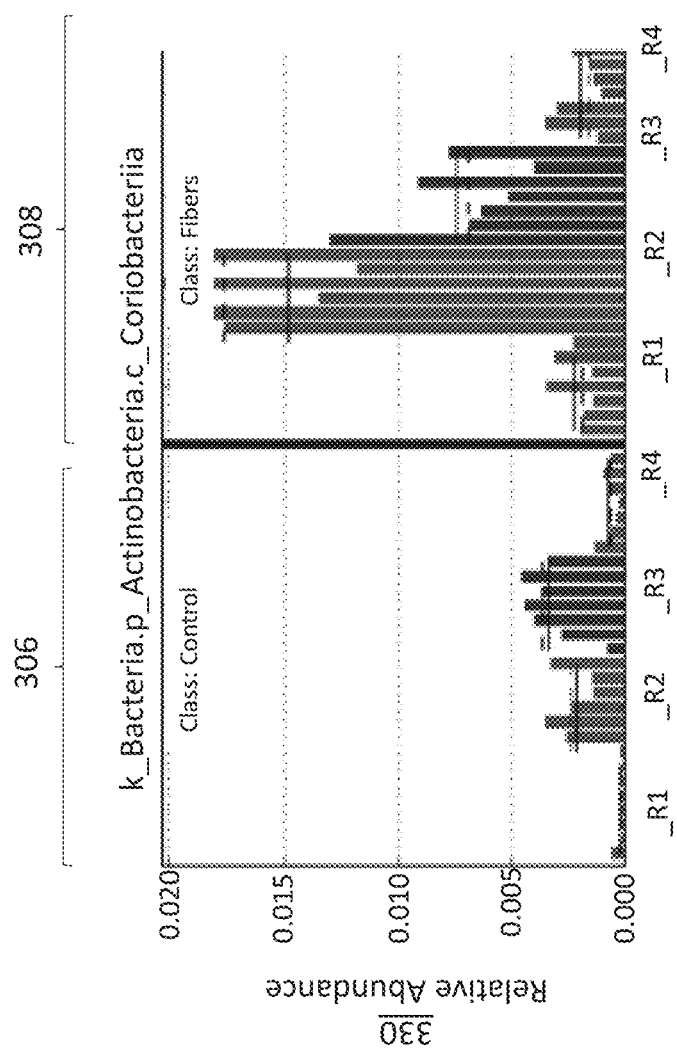
Figure 7I:
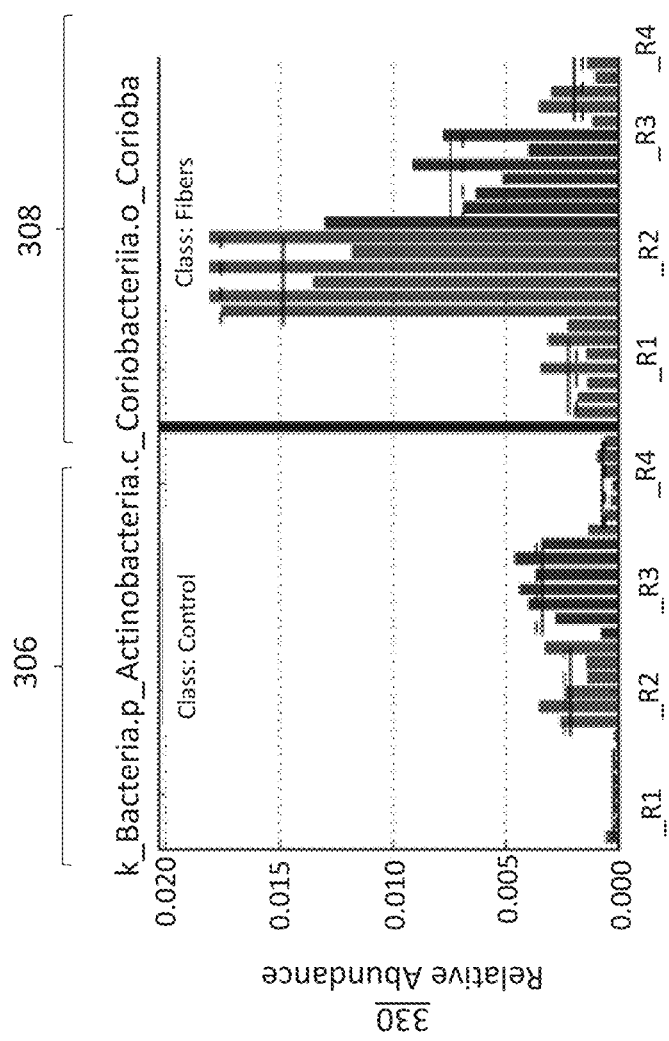
Figure 7J:
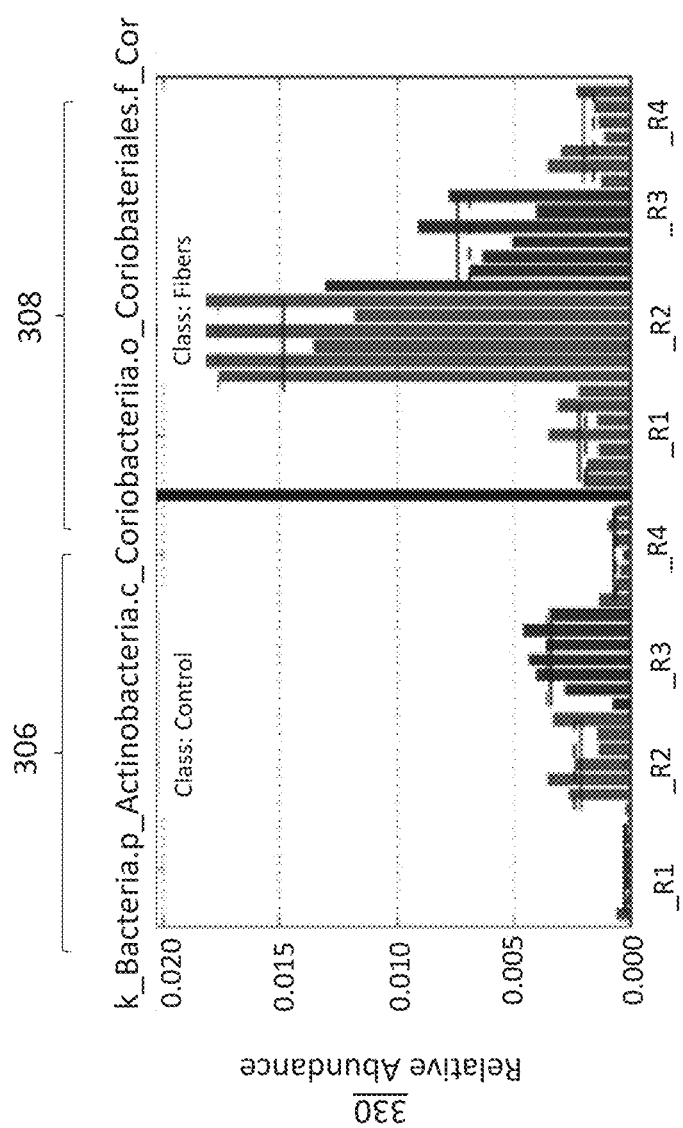

Finally, levels of Streptophyta, an order belonging to Cyanobacteria phylum, has been observed, had been significantly augmented with the probiotic powder of FIG. 1 (as shown in FIG. 5, FIG. 6, and FIG. 7G).

Example 18—Bifidobacterium Relative Abundance

Bifidobacterium is a genus of gram-positive, nonmotile, often branched anaerobic bacteria. Bifidobacterium are ubiquitous inhabitants of the gastrointestinal tract and mouth of mammals, including humans.

Figure 8A:
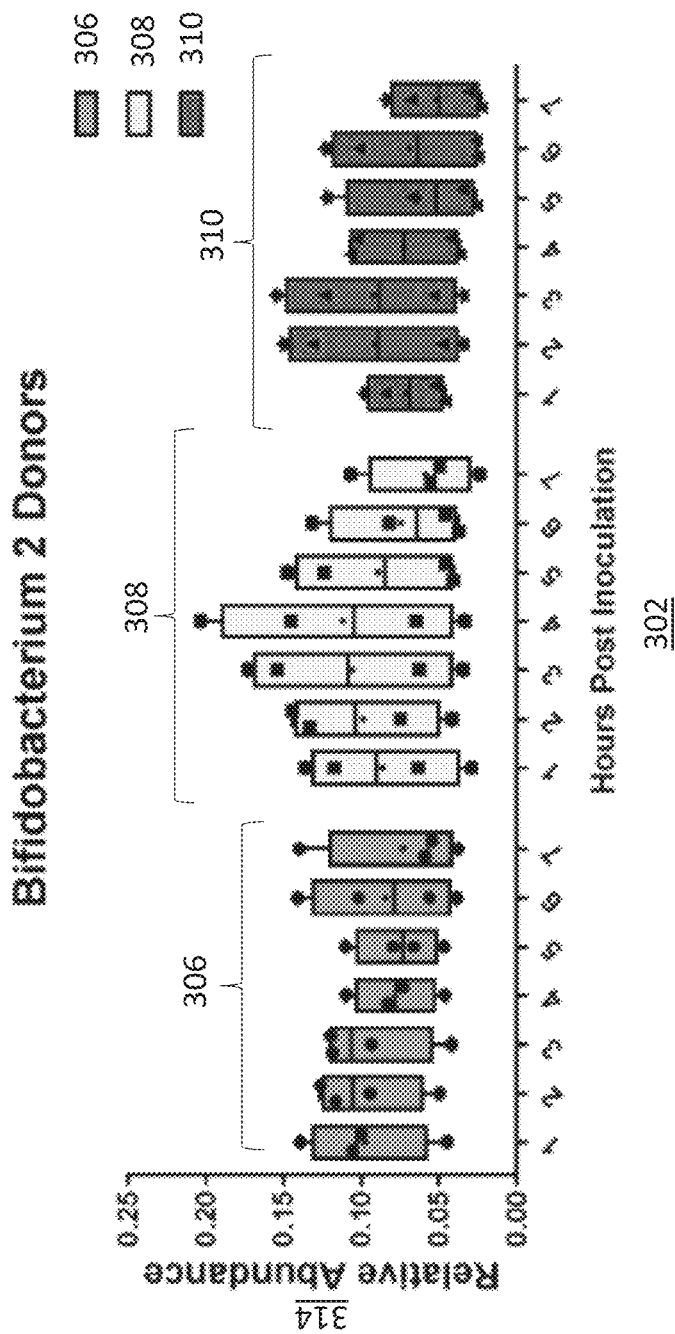
FIG. 8A-FIG. 8C depict graphical representations of *Bifidobacterium* relative abundance, according to at least some embodiments disclosed herein.
Figure 8B:
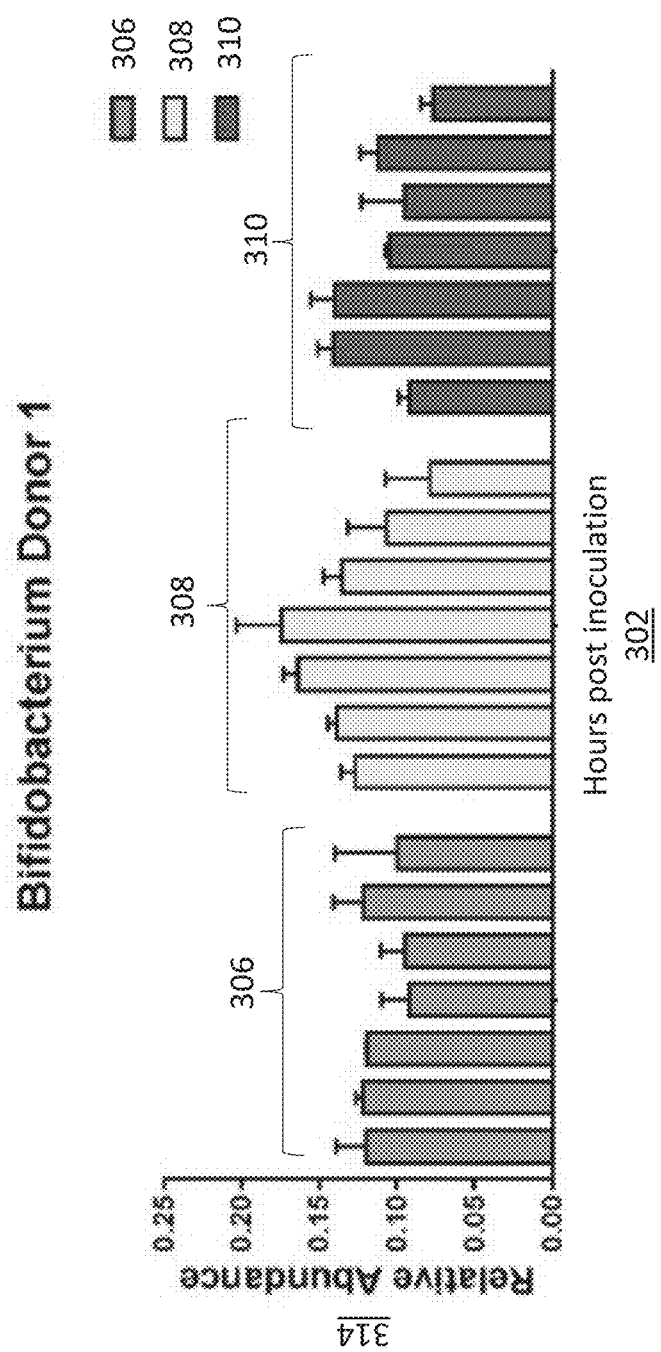
Figure 8C:
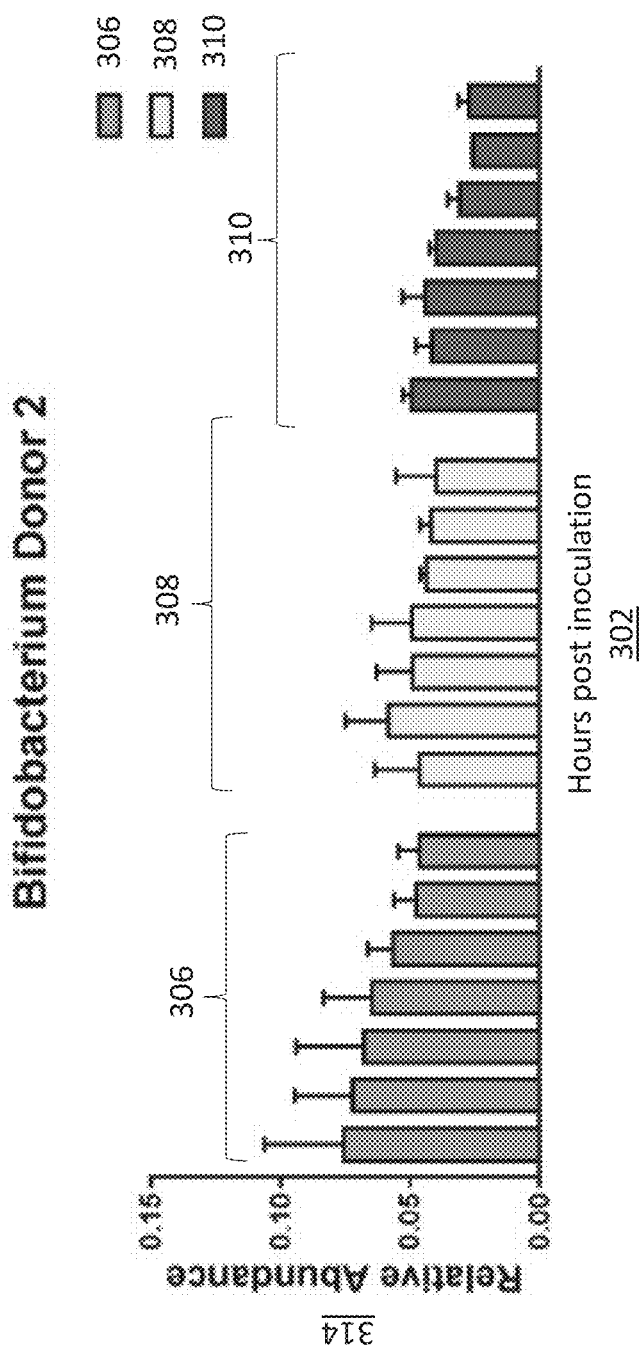

FIG. 8A, FIG. 8B, and FIG. 8C depict graphical representations of Bifidobacterium relative abundance on a graph having the x-axis representing hours post-inoculation 302 and the y-axis representing relative abundance 314. Specifically, the graphs of FIG. 8A-FIG. 8C depict the control 306, the fibers 308 of FIG. 1, and the MC cellulose 310.

As can be seen in FIG. 8A and FIG. 8B, the relative abundance of the Bifidobacterium associated with the control 306 is greatest after 6 hours post-inoculation, the relative abundance of the fibers 308 of FIG. 1 is greatest at 4 hours post-inoculation, and the relative abundance of the Bifidobacterium associated with the MC cellulose 310 is greatest at 2-3 hours post-inoculation.

As can be seen in FIG. 8C, the relative abundance of the Bifidobacterium associated with the control 306 is greatest after 1 hour post-inoculation, the relative abundance of the fibers 308 of FIG. 1 is greatest at 2 hours post-inoculation, and the relative abundance of the Bifidobacterium associated with the MC cellulose 310 is greatest at 1 hour post-inoculation. No significant difference was observed for the Bifidobacterium (as shown in FIG. 8A-FIG. 8C), which may be due to the low number of donors.

Example 19—Relative Abundance of Bacillus coagulans (BC30) in a Bioreactor after Addition of the Fibers of FIG. 1

Figure 9:
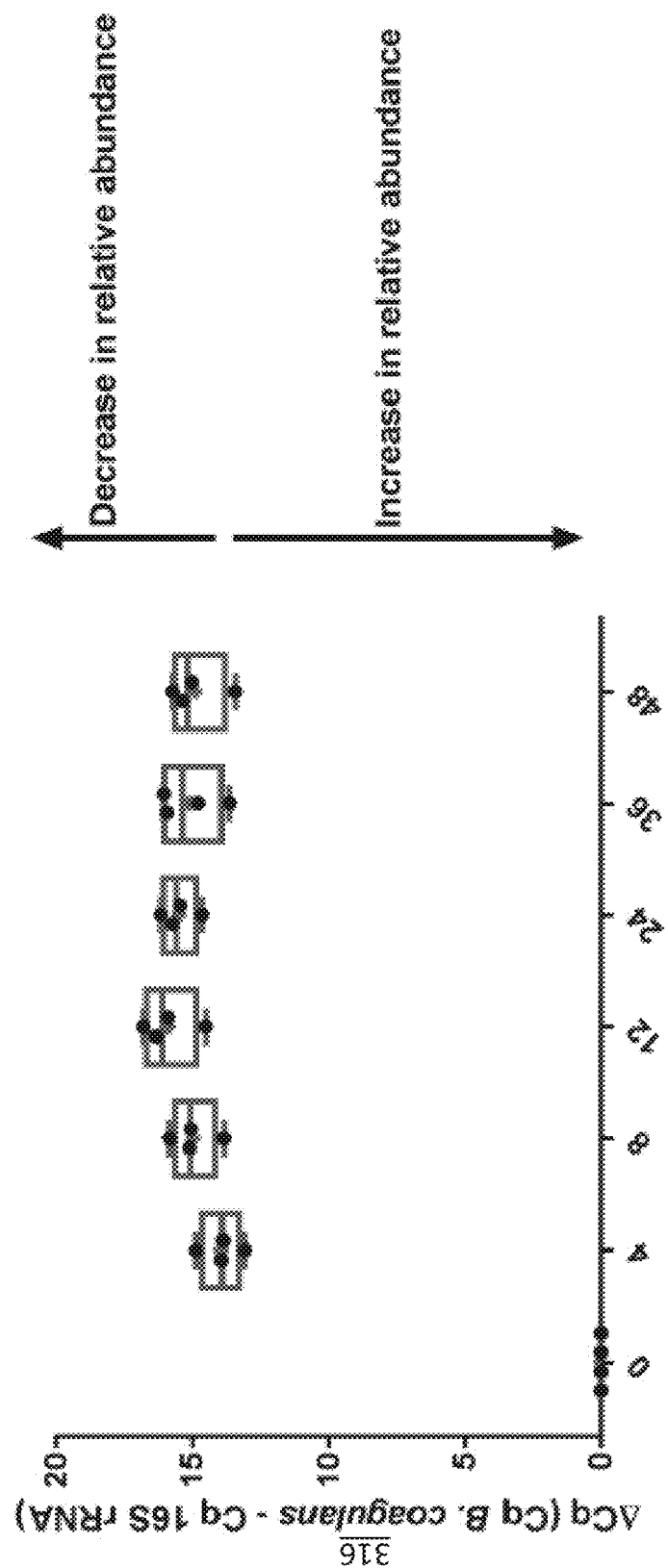
FIG. 9 depicts a graphical representation of a relative abundance of *Bacillus coagulans* in a bioreactor after addition of fibers of FIG. 1, according to at least some embodiments disclosed herein.

FIG. 9 depicts a graphical representation of a relative abundance of Bacillus coagulans (BC30) in a bioreactor after addition of the fibers of FIG. 1. As depicted in FIG. 9, the y-axis represents the ΔCq value or the cycle quantification value 316, which is the PCR cycle number at which the sample's reaction curve intersects the threshold line. This value tells one how many cycles it took to detect a real signal from the sample.

Example 20—Relative Abundance of Faecalibacterium prausnitzii in a Bioreactor after Addition of the Fibers of FIG. 1

FIG. 10 depicts a graphical representation of a relative abundance of Faecalibacterium prausnitzii associated with the control 306, the fibers 308 of FIG. 1, and the MC cellulose 310 in a bioreactor after addition of the fibers 308 of FIG. 1. As shown in FIG. 10, the x-axis represents the ΔCq value or the cycle quantification value 318 and the y-axis represents a quantity of hours post-inoculation 302. As can be seen in FIG. 10, Faecalibacterium prausnitzii did not show an increase after addition of the fibers 308 of FIG. 1.

Example 21—Short-Chain Fatty Acid (SCFA) Profiles

Figure 11A:
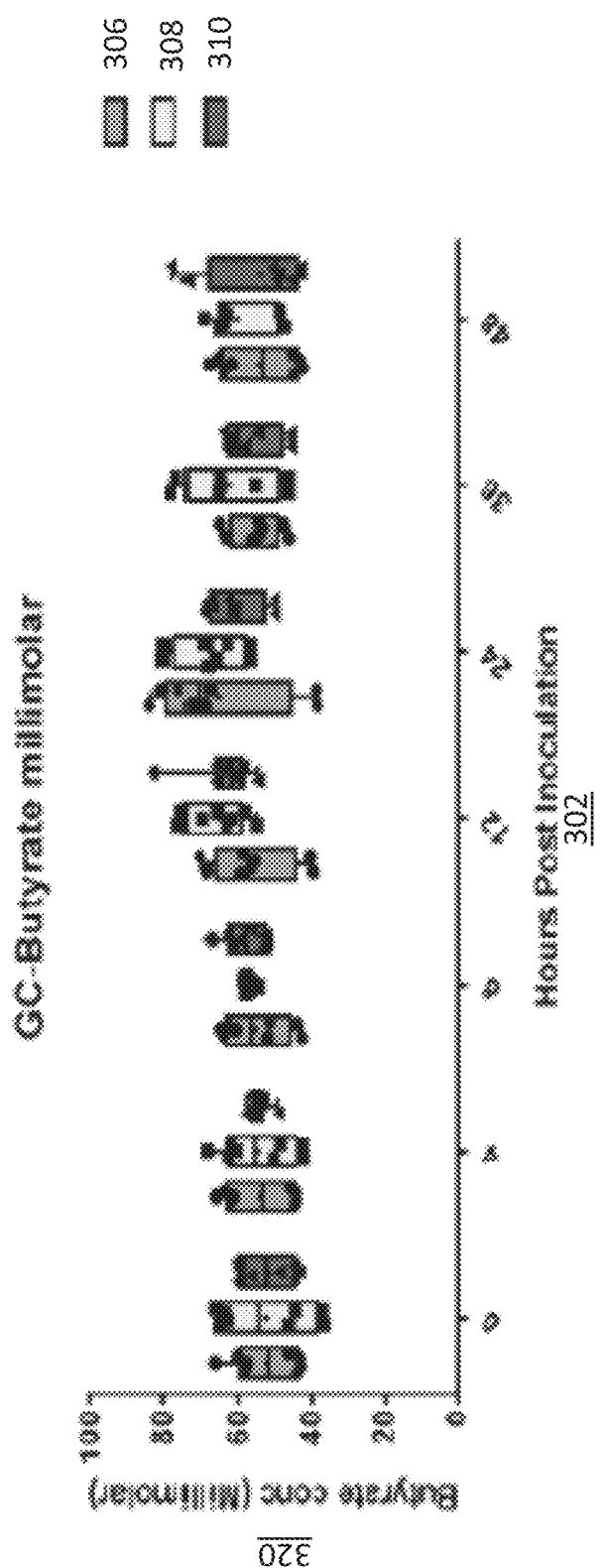
FIG. 11A, FIG. 11B, and FIG. 11C depict graphical representations of comparative short-chain fatty acid (SCFA) profiles, according to at least some embodiments disclosed herein.
Figure 11B:
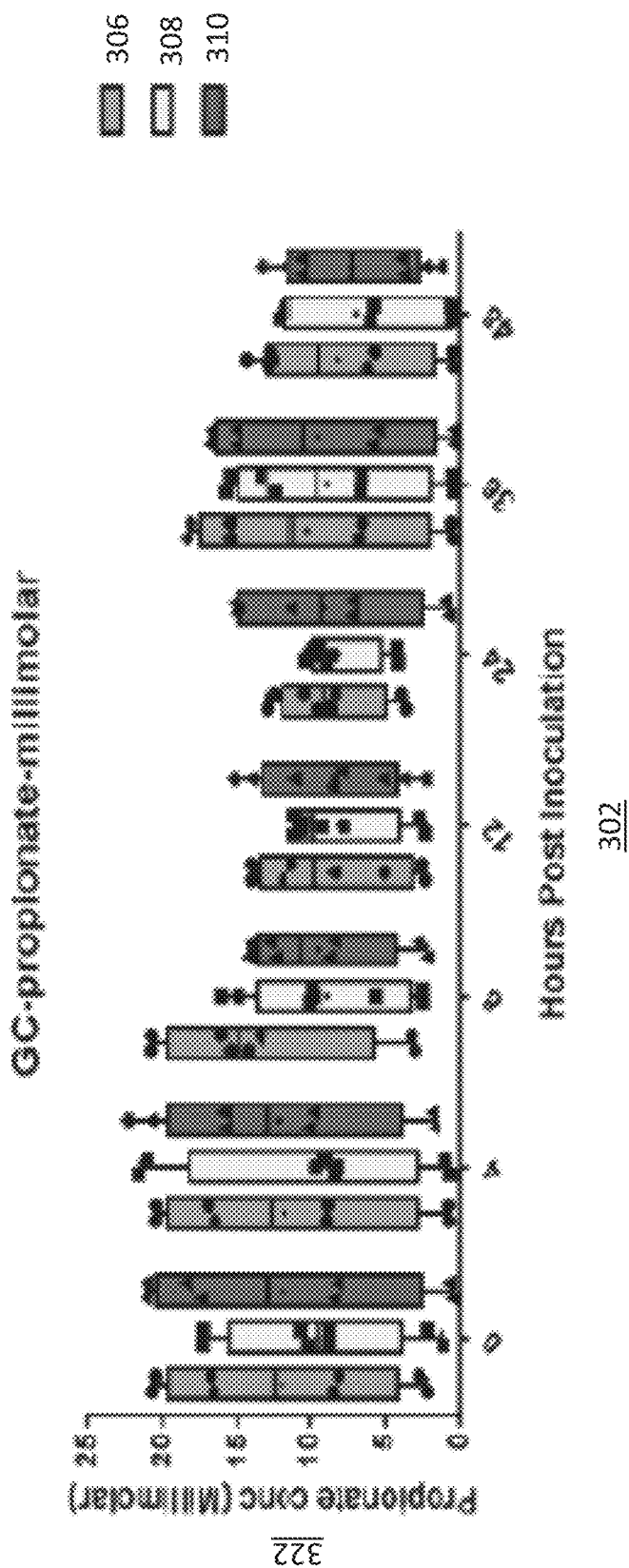
Figure 11C:
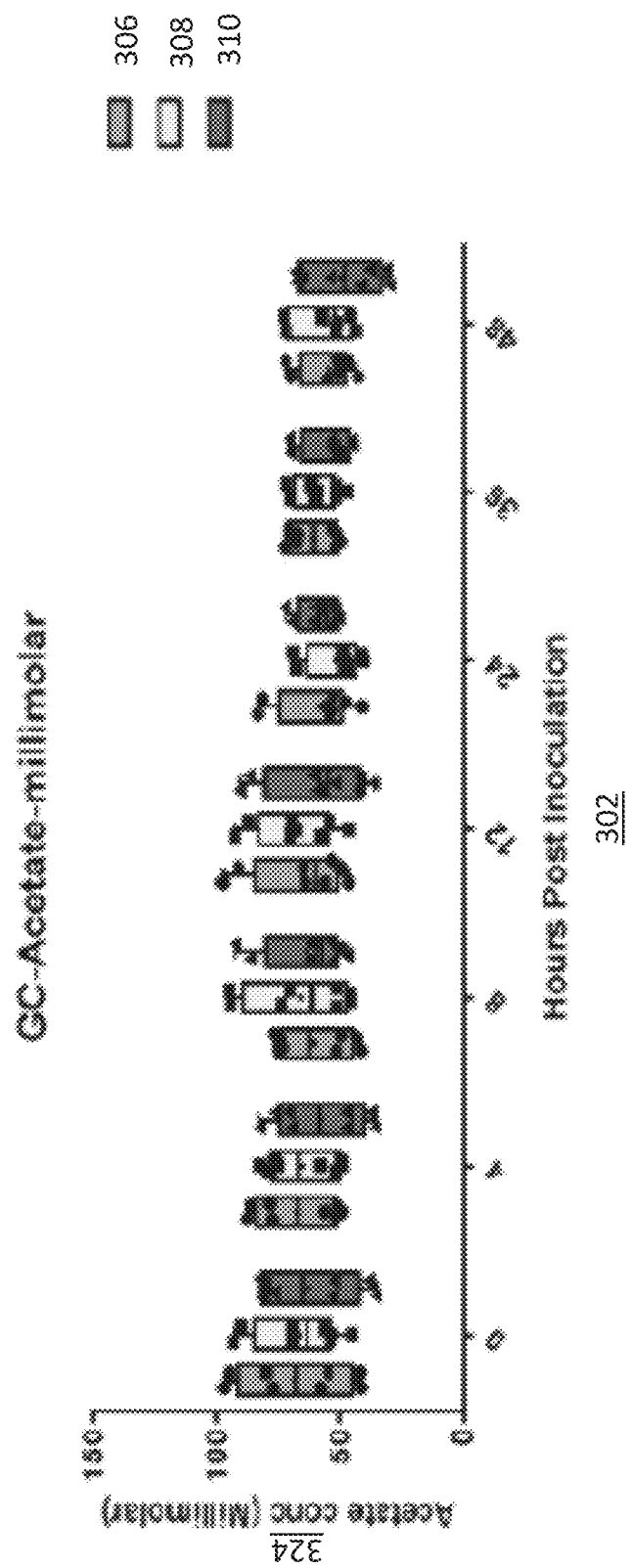

FIG. 11A-FIG. 11C depict graphical representations of comparative short-chain fatty acid (SCFA) profiles. Specifically, FIG. 11A depicts the control 306, the fibers 308 of FIG. 1, and the MC cellulose 310 on a graph having a quantity of hours post-inoculation 302 on the x-axis and butyrate concentration 320 in millimolar on the y-axis. FIG. 11B depicts the control 306, the fibers 308 of FIG. 1, and the MC cellulose 310 on a graph having the quantity of hours post-inoculation 302 on the x-axis and propionate concentration 322 in millimolar on the y-axis. FIG. 11C depicts the control 306, the fibers 308 of FIG. 1, and the MC cellulose 310 on a graph having the quantity of hours post-inoculation 302 on the x-axis and acetate concentration 324 in millimolar on the y-axis. Notably, based on FIG. 11A, addition of the fibers 308 of FIG. 1 increased the butyrate production.

Example 22—Butyrate Production Subsequent Addition of the Fibers 308 of FIG. 1

Butyrate production has been correlated with many health benefits to the gut, as well as the brain. See, Megan W. Bourassa, et al., "Butyrate, Neuroepigenetics and the Gut Microbiome: Can a High Fiber Diet Improve Brain Health?," Neurosci Lett., 2016, 625, Pages 56-63. The relationship between ones gut microbiota and nervous system is a large part of the gut-brain axis that has attracted increasing interest in recent years. It is estimated that 90% of the cells in the human body are of microbial origin, and the vast majority of these microbiota are comprised of 15,000-36,000 species of commensal and symbiotic bacteria that reside within the lumen of the gut. See, Daniel N. Frank, et al., "Molecular-phylogenetic characterization of microbial community imbalances in human inflammatory bowel diseases," Proc. Natl. Acad. Sci. U.S.A., 2007, 104(34), Pages 13780-13785; and R. M. Stilling, et al., "Microbial Genes, Brain & Behaviour—Epigenetic Regulation of the Gut-Brain Axis," Genes Brain Behav., 2014, 13(1), Pages 69-86.

Some studies have examined the effects of probiotics that would increase butyrate-producing bacteria. These studies showed that the probiotics reduced anxiety in rats and lowered psychological stress in human subjects. See, Michael Messaoudi, et al., "Assessment of Psychotropic-Like Properties of a Probiotic Formulation (Lactobacillus helveticus R0052 and Bifidobacterium longum R0175) in Rats and Human Subjects," Br. J. Nutr., 2011, 105(5), Pages 755-764. A similar study in subjects with chronic fatigue syndrome showed reduced anxiety, a common symptom of the disease, with the use of probiotics. See, A. Venket Rao, et al., "A randomized, double-blind, placebo-controlled pilot study of a probiotic in emotional symptoms of chronic fatigue syndrome," Gut Pathog., 2009, 1(6). Another study provided healthy subjects with a fermented milk product and used functional magnetic resonance imaging, functional MM, or fMRI to assess changes in the brain. See, Kristen Tillisch, et al., "Consumption of Fermented Milk Product With Probiotic Modulates Brain Activity," Gastroenterology, 2013, 144(7), Pages 1-15.

Figure 12:
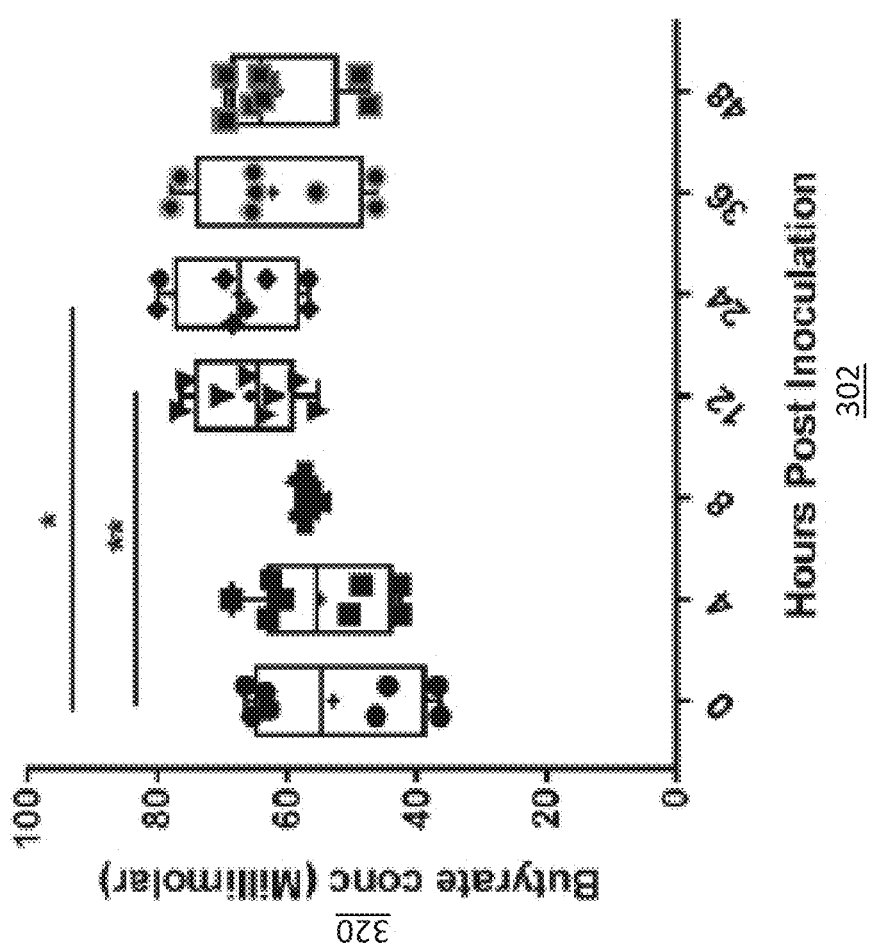
FIG. 12 depicts a graphical representation of butyrate increase after addition of fibers of FIG. 1 to a bioreactor, according to at least some embodiments disclosed herein.

A graph of FIG. 12 includes the quantity of hours post-inoculation 302 on the x-axis and the butyrate concentration 320 in millimolar on the y-axis. FIG. 12 depicts the butyrate increase after addition of the fibers 308 of FIG. 1 to a bioreactor. According to FIG. 12, addition of the fibers 308 of FIG. 1 increased the butyrate production by gut microbiota, and thus, may assist in reduction of anxiety and psychological stress in humans.

Example 23—Amino Acid Profile Analyses

Figure 13A:
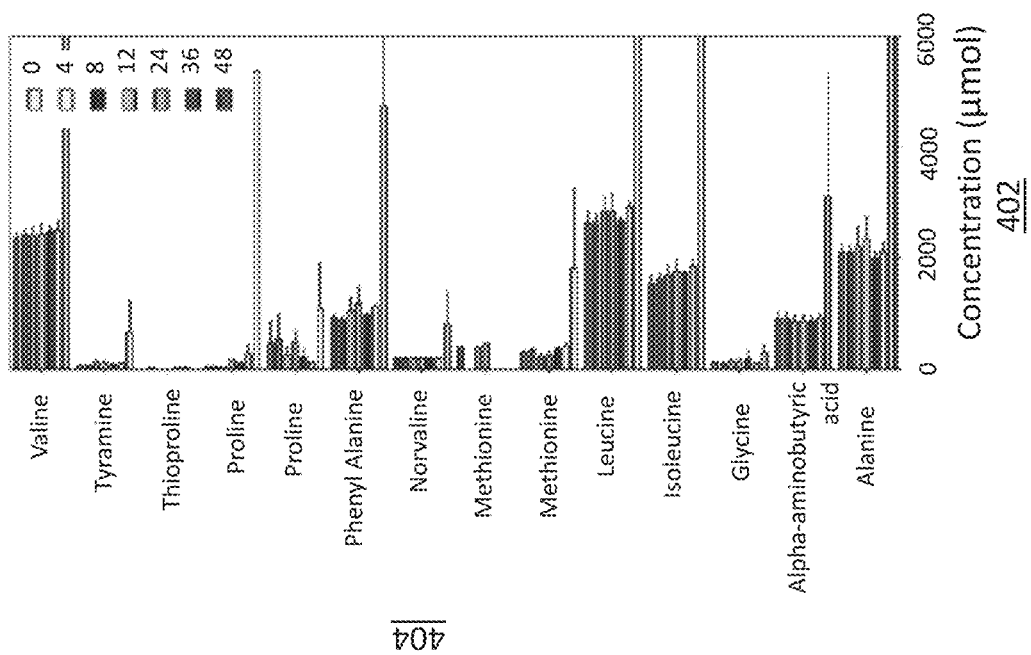
FIG. 13A depicts a graphical representation of amino acid profiles in view of a control, according to at least some embodiments disclosed herein.
Figure 13B:
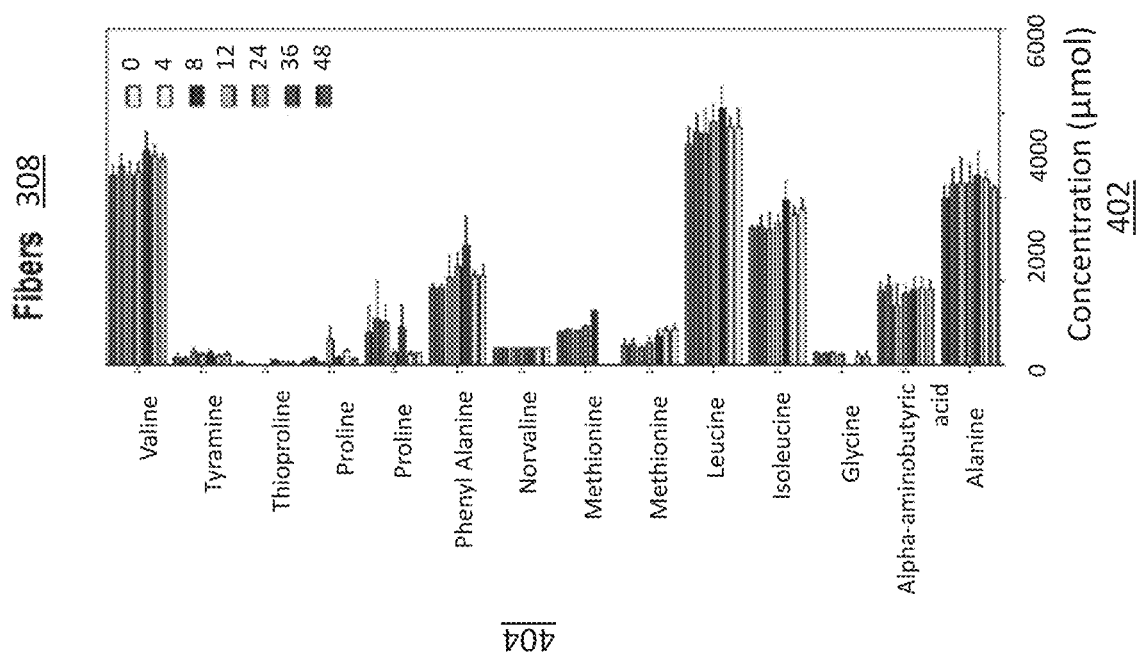
FIG. 13B depicts a graphical representation of amino acid profiles in view of the fibers of FIG. 1, according to at least some embodiments disclosed herein.
Figure 13C:
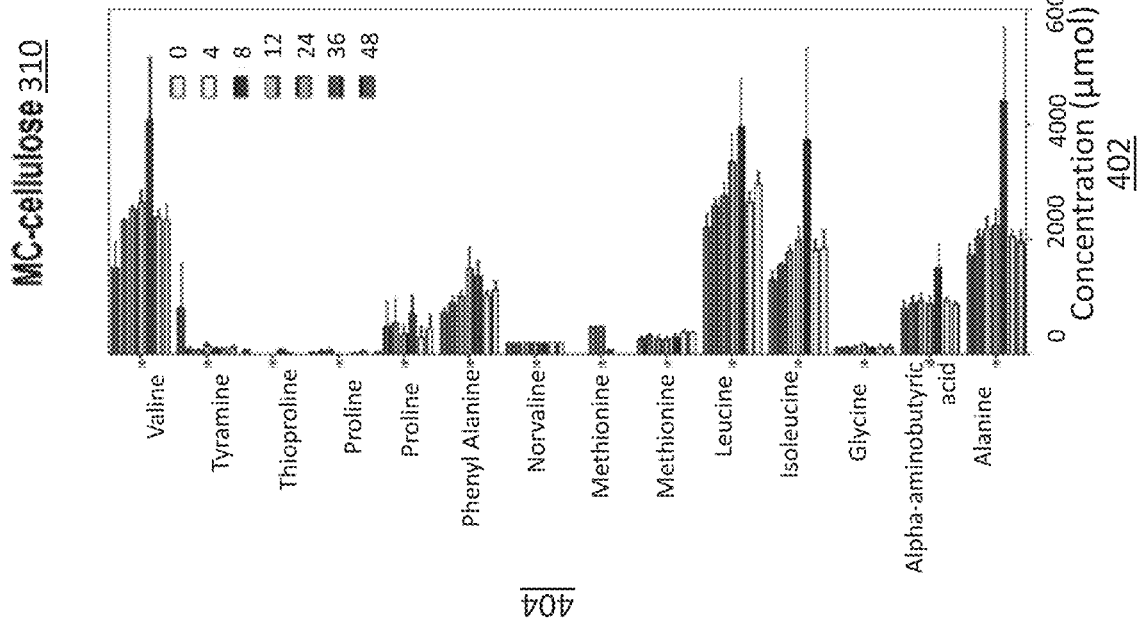
FIG. 13C depicts a graphical representation of amino acid profiles in view of microcrystalline (or MC) cellulose, according to at least some embodiments disclosed herein.

A graph of FIG. 13A, a graph of FIG. 13B, and a graph of FIG. 13C depict results of amino acid profile analyses. For FIG. 13A, FIG. 13B, and FIG. 13C, the x-axis represents concentration (in μmol) 402 and the y-axis represents amino acids 404. The amino acids profile analyses of FIG. 13A, FIG. 13B, and FIG. 13C did not detect or quantify difference in neurochemical production (e.g., GABA, dopamine, and serotonin) between treatment with the fibers 308 of FIG. 1 and the controls (before and after additions). However, an increased amount of valine, phenylalanine, leucine, isoleucine, alanine, and alpha-Aminobutyric acid (one of the three isomers of aminobutyric acid) was detected.

It should be appreciated that the examples are provided for illustrative purposes only. Moreover, cookies may be formed from any combination of (a) the baked food composition or the biscuit of Example 3, Example 5, Example 8, or Example 11 with (b) the crème filing composition of Example 4, Example 6, Example 9, or Example 12.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others or ordinary skill in the art to understand the embodiments disclosed herein.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A cookie for improving gut health, the cookie comprising:
   at least two biscuits, each of the at least two biscuits consisting of:
      a kiwi fruit powder;
      a toasted lupin flour;
      a resistant dextrin; and
      a vegetable fat; and
   a crème filing sandwiched between two of the at least two biscuits, the crème filling consisting of:
      a resistant dextrin;
      spores of a probiotic bacterium;
      a probiotic powder;
      one or more vegetable fats; and
      a nut butter,
   wherein the spores of the probiotic bacterium comprise spores of *Bacillus coagulans*, and
   wherein consumption of the cookie increases *Lactobacillus bulgaricus* and butyrate in a consumer.

2. The cookie of claim 1, wherein consumption of the cookie provides a prebiotic effect and/or a probiotic effect to a consumer.

3. A method for making a cookie that provides a prebiotic effect and/or a probiotic effect to a consumer, the method comprising:
   blending dry ingredients consisting of: a kiwi fruit powder, a resistant dextrin, and a toasted lupin flour with a vegetable fat;
   mixing in water until glomeration and formation of a dough;
   baking the dough to produce a baked food composition, wherein the baked food composition is a biscuit;
   sandwiching a crème filling between two of the biscuits to produce a cookie, wherein the crème filing is produced by the steps of:
      mixing vegetable fats to form a first mixture;
      mixing nut butter with a resistant starch to form a second mixture; and
      blending the first and second mixtures with a natural flavor and probiotic spores until glomeration of the crème filling, wherein the probiotic spores comprise spores of *Bacillus coagulans*.

4. A cookie that provides a prebiotic effect and/or a probiotic effect to a consumer, the cookie consisting of:
   at least two baked food compositions, wherein each of the at least two baked food compositions consists of:
      a kiwi fruit powder;
      a toasted lupin flour;
      a resistant dextrin; and
      a vegetable fat; and
   a crème filling sandwiched between two of the at least two baked food compositions, the crème filling consisting of:
      a resistant dextrin;
      spores of a probiotic bacterium;
      a probiotic powder;
      one or more vegetable fats; and
      a nut butter,
   wherein the spores of the probiotic bacterium comprise spores of *Bacillus coagulans*, and
   wherein consumption of the cookie increases *Lactobacillus bulgaricus* and butyrate in the consumer.

* * * * *